US010526601B2

(12) United States Patent
Xi et al.

(10) Patent No.: US 10,526,601 B2
(45) Date of Patent: Jan. 7, 2020

(54) HAPLOIDOME DETERMINATION BY DIGITIZED TRANSPOSONS

(71) Applicant: Digenomix Corporation, Foster City, CA (US)

(72) Inventors: Lei Xi, Foster City, CA (US); Xiaohui Wang, Foster City, CA (US); Marc Unger, San Mateo, CA (US); David Ruff, San Francisco, CA (US)

(73) Assignee: Digenomix Corporation, Foster City, CA (US)

( * ) Notice: Subject to any disclaimer, the term of this patent is extended or adjusted under 35 U.S.C. 154(b) by 630 days.

(21) Appl. No.: 14/719,149

(22) Filed: May 21, 2015

(65) Prior Publication Data

US 2015/0337298 A1 Nov. 26, 2015

Related U.S. Application Data

(60) Provisional application No. 62/002,733, filed on May 23, 2014.

(51) Int. Cl.
 *C12Q 1/68* (2018.01)
 *C12N 15/10* (2006.01)
 *C12Q 1/6806* (2018.01)

(52) U.S. Cl.
 CPC ..... *C12N 15/1082* (2013.01); *C12N 15/1065* (2013.01); *C12Q 1/6806* (2013.01)

(58) Field of Classification Search
 None
 See application file for complete search history.

(56) References Cited

U.S. PATENT DOCUMENTS

| 10,287,622 B2 * | 5/2019 | Belyaev | C12Q 1/6806 |
| 2010/0120098 A1 | 5/2010 | Grunenwald et al. | |
| 2012/0208705 A1 | 8/2012 | Steemers et al. | |
| 2013/0143745 A1 | 6/2013 | Christen et al. | |
| 2013/0203605 A1 * | 8/2013 | Shendure | C12N 15/1093 506/2 |
| 2013/0323732 A1 * | 12/2013 | Anderson | C12Q 1/6813 435/6.11 |

OTHER PUBLICATIONS

Robb et al. (Genes, Genomes and Genetics, 2013, vol. 3, p. 949-957).*
Jursch et al. (Mobile DNA, 2013, 4:15).*
Pobigaylo et al., "Construction of a Large Signature-Tagged Mini-Tn5 Transposon Library and Its Application to Mutagenesis of *Sinorhizobium meliloti*," *Applied and Environmental Microbiology*, (Jun. 2006), 72(6):4329-4337.
PCT/US2015/032066, International Search Report and Written Opinion, dated Nov. 26, 2015, pp. 1-10.
EP15727787.2, European Examination Report dated Feb. 12, 2018, 4 pages.

* cited by examiner

*Primary Examiner* — Stephanie K Mummert
(74) *Attorney, Agent, or Firm* — Kilpatrick Townsend & Stockton LLP

(57) ABSTRACT

In certain embodiments, the present invention provides a way of "digitally" marking different the alleles of different chromosomes by using a transposase to insert differently barcoded transposons into genomic DNA before further analysis. According to this method, each allele becomes marked with a unique pattern of transposon barcodes. Because each unique pattern of transposon barcodes identifies a particular allele, the method facilitates determinations of ploidy and copy number variation, improves the ability to discriminate among homozygotes, heterozygotes, and patterns arising from sequencing errors, and allows loci separated by uninformative stretches of DNA to be identified as linked loci, thereby facilitating haplotype determinations. Also provided is a novel artificial transposon end that includes a barcode sequence in two or more positions that are not essential for transposition.

22 Claims, 12 Drawing Sheets

Specification includes a Sequence Listing.

If Gene C is associated with three transposons, we know that it has three copies.

Fig. 3A

ADO or homozygote?

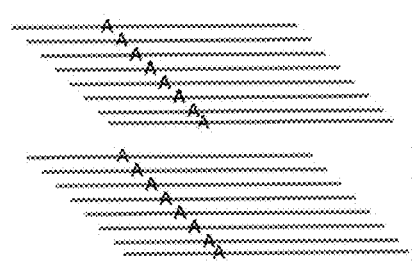 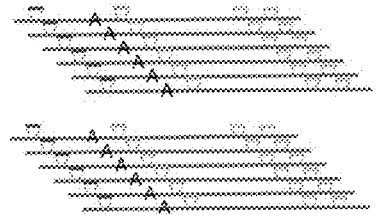

Huge coverage, but could be allele drop out

Huge coverage. Because of only one transposon pattern/sequence, there is high probability of ADO.

Existing

New

Fig. 3B

Two haploids may amplified to different level in WGA

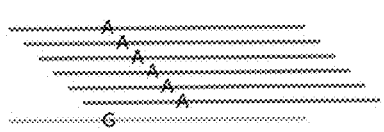 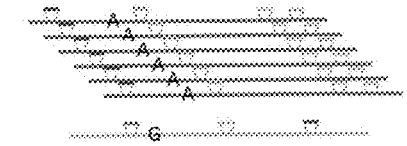

Is this sequencing error or heterozygote?

Probably heterozygote, as G-allele has low coverage as determined by the bar-coded transposons.

Existing

New

*Fig. 9A Chromosomal DNA*

```
ATCTGCTACCAGTCAACCCTAAAAATAGCCCATGATGTCACCCCAAGGCCTTCCCATTGGCTCGCGTCGCTCTCA      (SEQ ID NO:35)
          CAGTCAACCCTAAAAATAGCCCATGATGTCACCCCAAGGCCTTCCCATTGGCTCGCGTCGCTCGCTCTCAGGGGGCGG  (SEQ ID NO:36)
          CAGTCAACCCTAAAAATAGCCCATGATGTCACCCCAAGGCCTTCCCATTGGCTCGCGTCGCTCTCAGGGGGGCGG
```

*Fig. 9B Mitochondrial DNA*

```
AAATAGCCCACACGTTCCCCTTAAATAAGACATCACGATGGATCACAGGTCTATCACCCTATTAACCACTCACGGG                                           (SEQ ID NO:37)
AAATAGCCCACACGTTCCCCTTAAATAAGACATCACGATGGATCACAGGTCTATCACCCTATTAACCACTCACGGG
AAATAGCCCACACGTTCCCCTTAAATAAGACATCACGATGGATCACAGGTCTATCACCCTATTAACCACTCACGGG
   GCCCACACGTTCCCCTTAAATAAGACATCACGATGGATCACAGGTCTATCACCCTATTAACCACTCACGGGAGCTC                                        (SEQ ID NO:38)
   GCCCACACGTTCCCCTTAAATAAGACATCACGATGGATCACAGGTCTATCACCCTATTAACCACTCACGGGAGCTC
   GCCCACACGTTCCCCTTAAATAAGACATCACGATGGATCACAGGTCTATCACCCTATTAACCACTCACGGGAGCTC
   GCCCACACGTTCCCCTTAAATAAGACATCACGATGGATCACAGGTCTATCACCCTATTAACCACTCACGGGAGCTC
   GCCCACACGTTCCCCTTAAATAAGACATCACGATGGATCACAGGTCTATCACCCTATTAACCACTCACGGGAGCTC
      CACACGTTCCCCTTAAATAAGACATCACGATGGATCACAGGTCTATCACCCTATTAACCACTCACGGGAGCTCTCC                                     (SEQ ID NO:39)
         CCCTTAAATAAGACATCACGATGGATCACAGGTCTATCACCCTATTAACCACTCACGGGAGCTCTCCATGCATT   (SEQ ID NO:40)
           CCCTTAAATAAGACATCACGATGGATCACAGGTCTATCACCCTATTAACCACTCACGGGAGCTCTCCATGCATTT
           CCCTTAAATAAGACATCACGATGGATCACAGGTCTATCACCCTATTAACCACTCACGGGAGCTCTCCATGCATTT
           CCCTTAAATAAGACATCACGATGGATCACAGGTCTATCACCCTATTAACCACTCACGGGAGCTCTCCATGCATTT
           CCCTTAAATAAGACATCACGATGGATCACAGGTCTATCACCCTATTAACCACTCACGGGAGCTCTCCATGCATTTG
            TTAAATAAGACATCACGATGGATCACAGGTCTATCACCCTATTAACCACTCACGGGAGCTCTCCATGCATTTGGTA
             TAAATAAGACATCACGATGGATCACAGGTCTATCACCCTATTAACCACTCACGGGAGCTCTCCATGCATTTGGTA
             AAATAAGACATCACGATGGATCACAGGTCTATCACCCTATTAACCACTCACGGGAGCTCTCCATGCATTTGGTATT  (SEQ ID NO:41)
             AAATAAGACATCACGATGGATCACAGGTCTATCACCCTATTAACCACTCACGGGAGCTCTCCATGCATTTGGTATT  (SEQ ID NO:42)
             AAATAAGACATCACGATGGATCACAGGTCTATCACCCTATTAACCACTCACGGGAGCTCTCCATGCATTTGGTATT  (SEQ ID NO:43)
```

Ref: (SEQ ID NO: 44)

| Ref: | CTCTGTTTGT | CAAGTCTGCA | AGTGGATATT | CGGACCTCTT | TGAGGCCTTC | 27733039 |
|---|---|---|---|---|---|---|
| Seq1 | ---------- | a--c------ | ---------- | c--------- | ---------- | |
| Seq2 | ---------- | ---------- | ---------- | --A------- | --------aa | |
| Seq3 | ---------- | ---------- | ---------- | --A------- | ---------- | |
| Seq4 | ---------- | ---------- | ---------- | --A------- | ---------- | |

| Ref: | GTTGGAAACG | GGATTTCTTC | ATAtTAcaCT | AGACAGAAGA | ATTCTCAGTA | 27733089 |
|---|---|---|---|---|---|---|
| Seq1 | ---------- | ---------- | ---c------ | ---------- | ---------- | |
| Seq2 | ---------- | ----t----- | ---c--tg-- | ---------- | ---------- | |
| Seq3 | ---------- | ----t----- | ---a--tg-- | ---------- | ----c----- | |
| Seq4 | ---------- | ---------- | ---c--tg-- | ---------- | ---------- | |

| Ref: | ACTTCCTTTT | GTTGTGTGTA | TTCAACTGAC | AGAGTTGAAC | CTTCCCTTAG | 27733139 |
|---|---|---|---|---|---|---|
| Seq1 | ---------- | ---------- | (SEQ ID NO: 45) | | | |
| Seq2 | ---------g | ---------- | (SEQ ID NO: 46) | | | |
| Seq3 | ---------- | ---------- | (SEQ ID NO: 47) | | | |
| Seq4 | ---------- | ---------- | (SEQ ID NO: 48) | | | |

*Fig. 10*

HAPLOIDOME DETERMINATION BY DIGITIZED TRANSPOSONS

CROSS-REFERENCE TO RELATED APPLICATIONS

This application claims the benefit of U.S. provisional application No. 62/002,733, filed May 23, 2014, which is hereby incorporated by reference in its entirety.

STATEMENT AS TO RIGHTS TO INVENTIONS MADE UNDER FEDERALLY SPONSORED RESEARCH AND DEVELOPMENT

Not applicable.

SEQUENCE LISTING

The instant application contains a Sequence Listing which has been submitted electronically in ASCII format and is hereby incorporated by reference in its entirety. Said ASCII copy, created on Jul. 28, 2015, is named FLUDP015US_SL.txt and is 15,254 bytes in size.

FIELD OF THE INVENTION

The present invention relates to generally to the area of haploidome determination using transposons. In particular embodiments, the invention relates to methods and compositions for complete haploidome determination at high resolution from single cells using digitized transposons.

BACKGROUND OF THE INVENTION

It has been well documented that whole genome amplifications, either by PCR-based or by isothermal amplification, generally leads to biased amplification, resulting in that some areas are over-amplified, while other areas are under-amplified. This bias makes copy number variation (CNV) difficult to determine and single nucleotide polymorphisms (SNPs) or single nucleotide variations (SNVs; i.e., mutations) challenging to identify or "call."

Various computer programs have been employed to help to solve these problems. However, due to the chaotic nature of amplification, it is often difficult to determine whether an observed CNV is genuine or an artifact of amplification. In addition, most computer programs operate on the assumption that each genome consists of 44 euchromosomes and two sex chromosomes, which is not the case for all cells, and certainly not the case for cancer cells, which can exhibit vast differences in copy number among cells within a cancer cell line and within a cancer tissue.

In particular, karyotyping studies have found that some normal mammalian cells are of high ploidy. A single cell could contain 4, 6, 8, or up to hundreds' of full sets of chromosomes. These cells have uniformly changed copy numbers throughout the genome. Therefore, the absolute copy number cannot be determined for these cells using conventional sequencing methods or PCR, as these methods all rely on at least one reference point on the chromosome, be it a gene, or a segment, or a whole chromosome.

Karyotypes of tumor cells in tumor tissues or in established tumor cell lines tends to be even more complex and heterogeneous. Chromosome numbers tend to vary from less than 46 (hypoploid) to 92 (tetraploid). Adding to the complexity, tumor cells within an established tumor cell line, or within a tumor tissue, consist of a collection of cells of different chromosome numbers, and a particular chromosome, e.g. Chromosome 1, could exist as 1 copy, or 2, or 5, or 6, or 7 in one cell, but be missing in another cell. Therefore, for a tumor cell line like this, the average copy number of Chromosome 1 may be a fraction. Mutation "calls" for situations like this are extremely challenging, as one mutation on one of seven Chromosome 1's will be represented by 14% of reads.

Moreover, in the detection of rare mutations in cancer studies, even with the help of "deep sequencing." the typical error rate of ~1% in sequencing usually results in hundreds of millions of sequencing mistakes. These scattered errors can be tolerated in some applications, but become extremely problematic in the identification of ultra-rare mutations in populations of cells, as well as in single cells, if the rare mutation occurred in a minor allele.

SUMMARY OF THE INVENTION

In various aspects, the invention(s) contemplated herein may include, but need not be limited to, any one or more of the following embodiments:

Embodiment 1

A kit including a set of two or more transposons, wherein each transposon includes a different first transposon barcode sequence and transposon ends flanking a stuffer sequence, wherein the transposons each comprise the same first primer binding site in the stuffer sequence and are capable of being inserted into nucleic acids by a transposase.

Embodiment 2

The kit of embodiment 1, wherein the first transposon barcode sequence is located within or adjacent to a transposon end.

Embodiment 3

The kit of embodiments 1 or 2, wherein each transposon additionally includes a second transposon barcode sequence.

Embodiment 4

The kit of embodiment 3, wherein the second transposon barcode sequence is located within or adjacent to a transposon end, and wherein the first transposon barcode sequence is located within or adjacent to the other transposon end.

Embodiment 5

The kit of embodiments 1-4, wherein the transposon additionally includes a first index sequence, and wherein the kit includes sets of two or more transposons, wherein each transposon within the set includes a different first transposon barcode sequence, and each set of transposons is characterized by a different index sequence.

Embodiment 6

The kit of embodiments 1-5, wherein the first index sequence is adjacent to the first barcode or transposon end.

Embodiment 7

The kit of embodiments 5 and 6, wherein each transposon additionally includes a second index sequence.

Embodiment 8

The kit of embodiment 7, wherein each transposon includes: the first transposon barcode sequence located within or adjacent to one transposon end, and a second transposon barcode sequence located within or adjacent to the other transposon end; wherein the first index sequence is adjacent to the first barcode sequence, and the second index sequence is adjacent to the second barcode sequence.

Embodiment 9

The kit of any of embodiments 1-8, wherein the first primer binding site is located in the stuffer sequence and includes a site suitable for priming whole genome amplification (WGA).

Embodiment 10

The kit of embodiments 1-9, wherein each transposon additionally includes a second primer binding site.

Embodiment 11

The kit of embodiment 10, wherein the second primer binding site is located inside of the first transposon barcode sequence and the first index sequence, if present, wherein the second primer binding site includes a site suitable for priming DNA sequencing.

Embodiment 12

The kit of embodiment 4, wherein each transposon additionally includes a third primer binding site.

Embodiment 13

The kit of embodiment 12, wherein the third primer binding site is located inside of the second transposon barcode sequence and a second index sequence, wherein the third primer binding site includes a site suitable for priming DNA sequencing.

Embodiment 14

The kit of embodiment 12, wherein each transposon includes: the first transposon barcode sequence located within or adjacent to one transposon end, and a second transposon barcode sequence located within or adjacent to the other transposon end; wherein: a first index sequence is adjacent to the first barcode sequence; a second index sequence is adjacent to the second barcode sequence; the first primer binding site is located in the stuffer sequence; the second primer binding site is located inside of the first barcode sequence and the first index sequence; and the third primer binding site is located inside of the second barcode sequence and the second index sequence.

Embodiment 15

The kit embodiments 12-14, wherein the second and third primer binding sites are the same.

Embodiment 16

The kit of embodiments 1-15, wherein the stuffer sequence is double-stranded.

Embodiment 17

The kit of embodiment 16, wherein the stuffer sequence is at least 400 nucleotides long.

Embodiment 18

The kit of embodiments 1-15, wherein the stuffer sequence is single-stranded.

Embodiment 19

The kit of embodiment 18, wherein the stuffer sequence is at least 45 nucleotides long.

Embodiment 20

The kit of embodiments 1-19, wherein the two or more transposons are single-stranded transposons.

Embodiment 21

A method of marking sample nucleic acids, the method including: contacting sample nucleic acids derived from 10 or fewer cells with a loaded transposase capable of incorporating transposons into the sample nucleic acids; thereby forming nucleic acid molecules, wherein particular transposons are associated with particular nucleic acid segments; and detecting the number of different transposon-nucleic acid segment combinations that comprise at least one locus.

Embodiment 22

The method of embodiment 21, wherein the different transposon-nucleic acid segment combinations comprise the same transposon sequence inserted at different sites.

Embodiment 23

The method of embodiment 21, wherein the different transposon-nucleic acid segment combinations comprise different transposon sequences inserted by different transposases.

Embodiment 24

The method of embodiment 21, wherein the transposons comprise a set of two or more transposons, wherein: each transposon includes a different first transposon barcode sequence; said contacting forms barcoded nucleic acid molecules, wherein particular transposon barcodes are associated with particular nucleic acid segments; and said detecting includes detecting the number of different barcode-nucleic acid segment combinations that comprise at least one locus.

Embodiment 25

The method of embodiments 21-24, wherein the transposons comprise single-stranded transposons.

Embodiment 26

The method of embodiment 24, wherein the transposons comprise transposons from the kit of embodiments 1-20.

Embodiment 27

The method of embodiments 24 or 26, wherein the method includes incorporating at least 10 different barcodes into the sample nucleic acids.

Embodiment 28

The method of embodiments 21-27, wherein the sample nucleic acids comprise genomic DNA derived from no more than a single cell.

Embodiment 29

The method of embodiments 21-28, wherein the method includes incorporating, on average, one transposon every 500 base pairs of genomic DNA.

Embodiment 30

The method of embodiments 21-29, wherein a subset of the sample nucleic acids is sufficiently accessible to the loaded transposase to permit transposition and another subset is not sufficiently accessible to the loaded transposase to permit transposition.

Embodiment 31

The method of embodiment 30, wherein the sample nucleic acids comprise chromatin, and the subset of sample nucleic acids that is sufficiently accessible to the loaded transposase to permit transposition includes nucleic acids in an open configuration in the chromatin.

Embodiment 32

The method of embodiment 30, wherein the sample nucleic acids comprise chromatin with associated methyl-CpG-binding domain (MBD) proteins, and the subset of sample nucleic acids that is not sufficiently accessible to the loaded transposase to permit transposition includes nucleic acids in CpG islands.

Embodiment 33

The method of embodiments 21-32, wherein the method additionally includes performing whole genome amplification of the nucleic acid molecules.

Embodiment 34

The method of embodiments 21-33, wherein said detecting includes DNA sequencing.

Embodiment 35

The method of embodiments 21-34, wherein the sample nucleic acids comprise genomic DNA, and the method includes detecting the number of different transposon-nucleic acid segment combinations that comprise at least one locus to determine the copy number of that locus.

Embodiment 36

The method of embodiment 35, wherein when the detected number of different transposon-nucleic acid segment combinations is greater than the expected normal number of alleles for the locus, the sample is identified as one wherein the locus is at a higher than expected copy number in the cell.

Embodiment 37

The method of embodiment 35, wherein when the detected number of different transposon-nucleic acid segment combinations is less than the expected normal number of alleles for the locus, the sample is identified as one wherein either the locus is at a lower than expected copy number in the cell or allele-dropout may have occurred during amplification and/or sequencing.

Embodiment 38

The method of embodiment 35, wherein when the detected transposon-nucleic acid segment combinations comprise two different combinations wherein a nucleic acid segment including the same nucleic acid sequence at the locus is associated with one or more transposons at different insertion sites, one or more different transposon sequences, and/or one or more different barcodes, combinations thereof, the sample is identified as diploid and homozygous for the locus.

Embodiment 39

The method of embodiment 35, wherein when the detected transposon-nucleic acid segment combinations comprise two different transposon-nucleic acid segment combinations wherein nucleic acid segments including different nucleic acid sequences at the locus are each associated with one or more transposons at different insertion sites, one or more different transposon sequences, and/or one or more different barcodes, combinations thereof, the sample is identified as diploid and heterozygous for the locus.

Embodiment 40

The method of embodiment 34, wherein when the detected transposon-nucleic acid segment combinations comprise two different transposon-nucleic acid segment combinations wherein nucleic acid segments including different nucleic acid sequences at the locus are each associated with the same transposons or barcodes at the same insertion sites, the sample is identified as one in which an error may have been introduced into the sample nucleic acid sequence during amplification or sequencing.

Embodiment 41

The method of embodiment 34, wherein when the detected transposon-nucleic acid segment combinations comprise two or more different transposon-nucleic acid segment combinations wherein nucleic acid segments including different nucleic acid sequences at the locus are each associated with one or more transposons at different insertion sites, one or more different transposon sequences, and/or one or more different barcodes, combinations thereof, the sample is identified as one that includes a sequence difference at the locus.

Embodiment 42

The method of any of embodiments 36-41, wherein the transposons comprise barcodes, and said detection of the transposon-nucleic acid segment combinations includes detection of barcode-nucleic acid segment combinations.

Embodiment 43

The method of embodiment 35, wherein the method includes determining genome-wide copy number variation at—less than 10 kilobase resolution, on average.

Embodiment 44

The method of embodiment 43, wherein the method includes determining genome-wide copy number variation at an approximately 500 base resolution, on average.

Embodiment 45

The method of embodiments 21-34, wherein the method additionally includes determining whether two separated loci are present on the same chromosome, wherein one or more transposons is/are incorporated into intervening sample nucleic acid sequences to produce a transposon-nucleic acid segment combination, and the method additionally includes analyzing the loci to determine whether both loci are linked with the same transposon-nucleic acid segment combination, wherein a determination that the loci are linked with the same transposon-nucleic acid segment combination indicates that the loci are present on the same chromosome.

Embodiment 46

The method of embodiment 45, the method additionally includes detecting the number of different transposon-nucleic acid segment combinations that are linked to both loci to determine the copy number of the segment of genomic DNA containing both loci.

Embodiment 47

The method of embodiments 21-34, wherein: said contacting includes contacting the sample nucleic acids in a first condition with the loaded transposase in a first round of transposition to form a first set of nucleic acid molecules, wherein particular first transposons are associated with particular nucleic acid segments; and the method additionally includes: subjecting the first set of nucleic acid molecules, in a second condition, to a second round of transposition to form a second set of nucleic acid molecules, wherein particular second transposons are associated with particular nucleic acid segments, the second transposons being different from the first transposons; and for at least one locus, detecting: the number of different transposon-nucleic acid segment combinations that comprise first transposons; and the number of different transposon-nucleic acid segment combinations that comprise second transposons.

Embodiment 48

The method of embodiment 47, wherein: the sample nucleic acids in the first condition includes chromatin; the first set of nucleic acid molecules in the second condition includes purified DNA; the different transposon-nucleic acid segment combinations that comprise first transposons identify different alleles having an open configuration in the chromatin; and the different transposon-nucleic acid segment combinations that comprise second transposons identify different alleles having an open configuration in the chromatin.

Embodiment 49

The method of embodiment 48, wherein the sample nucleic acids comprise a wildtype allele and a mutant allele for the locus, and the analysis is carried out to determine whether the wildtype allele has an open configuration in the chromatin.

Embodiment 50

The method of embodiments 48 or 49, wherein the method additionally includes, for at least a second locus, detecting: the number of different transposon-nucleic acid segment combinations that comprise first transposons; and the number of different transposon-nucleic acid segment combinations that comprise second transposons.

Embodiment 51

The method of embodiment 50, wherein the method additionally includes determining whether the two loci are present on the same chromosome, wherein a plurality of first/and or second transposons is incorporated into intervening sample nucleic acid sequences, and the method additionally includes analyzing the loci to determine whether they are linked with the same plurality of transposons, wherein a determination that the loci are linked with the same plurality of transposons indicates that the loci are present on the same chromosome.

Embodiment 52

The method of embodiments 50 or 51, wherein the first locus includes a structural gene and the second locus includes a regulatory gene for that structural gene.

Embodiment 53

The method of embodiments 49-52, wherein the at least one locus or the first locus includes a tumor suppressor gene.

Embodiment 54

An artificial transposon end including a sequence wherein at least 2 nucleotides of the corresponding wildtype transposon end sequence have each been substituted with a different nucleotide.

Embodiment 55

The artificial transposon end of embodiment 54, wherein the wildtype transposon end sequence includes a single-stranded transposon end sequence.

Embodiment 56

A kit including a set of two or more different first artificial transposon ends, each including a sequence wherein at least 2 nucleotides of the corresponding wildtype transposon end sequence have each been substituted with a different nucleotide, said substitutions defining a barcode, wherein different first artificial transposon ends comprise different barcodes.

Embodiment 57

The kit of embodiment 56, wherein the wildtype transposon end sequence includes a single-stranded transposon end sequence.

Embodiment 58

The kit of embodiment 56, wherein different artificial transposon ends are packaged separately from one another.

Embodiment 59

The kit of embodiments 56 or 57, wherein the kit additionally includes a transposase capable of incorporating the first artificial transposon ends into the sample nucleic acids.

Embodiment 60

The kit of embodiment 59, wherein different first artificial transposon ends are packaged separately from one another, and the transposase is packaged with each different artificial transposon end.

Embodiment 61

The kit of any of embodiments 56-60, wherein the kit additionally includes a second transposon end, wherein the transposase is additionally capable of incorporating the second transposon end into the sample nucleic acids, thereby forming a tagged nucleic acid molecule wherein the first and second transposon ends flank and are separated by the sample nucleic acid sequence.

Embodiment 62

The kit of embodiment 61, wherein the second transposon end includes a nucleotide sequence different from that any of the first artificial transposon end.

Embodiment 63

The kit of embodiments 61 or 62, wherein the second transposon end includes a second artificial transposon end including a sequence wherein at least 2 nucleotides of the corresponding wildtype transposon end sequence have each been substituted with a different nucleotide, said substitutions defining a barcode.

Embodiment 64

The kit of embodiment 63, wherein the kit includes a set of second artificial transposon ends, wherein different second artificial transposon ends have different barcodes.

Embodiment 65

The kit of embodiments 56-60, wherein the kit additionally includes a primer that binds within the artificial transposon ends and primes polymerization of a nucleotide sequence including the barcode, wherein a plurality of the different artificial transposon ends includes the same primer binding site.

Embodiment 66

The kit of embodiments 56-65, wherein the barcode includes at least 3 nucleotides.

Embodiment 67

The kit of embodiments 56-66, wherein the barcode nucleotides are adjacent to one another.

Embodiment 68

The kit of embodiment 67, wherein kit includes a primer that binds within the artificial transposon end at a site adjacent to the barcode and primes polymerization of a nucleotide sequence including the barcode, which is adjacent to any invariant transposon end nucleotide(s), which is/are adjacent to the sample nucleic acid sequence.

Embodiment 69

A method of producing a tagged nucleic acid molecule, the method including contacting sample nucleic acids with a loaded transposase, wherein the transposase is loaded with a first artificial transposon end including a sequence wherein at least 2 nucleotides of the corresponding wildtype transposon end sequence have each been substituted with a different nucleotide, said substitutions defining a barcode, wherein the loaded transposase is capable incorporating the first artificial transposon end into the sample nucleic acids; and thereby forming a tagged nucleic acid molecule including the first artificial transposon end flanking a sample nucleic acid segment.

Embodiment 70

The method of embodiment 69, wherein the wildtype transposon end includes a single-stranded transposon end, and the transposase includes a single-stranded transposase.

Embodiment 71

The method of embodiment 69, wherein the method additionally includes: contacting the sample nucleic acids with a second transposon end, wherein the transposase is additionally capable of incorporating the second transposon end into the sample nucleic acids; and thereby forming a tagged nucleic acid molecule wherein the first and second transposon ends flank and are separated by the sample nucleic acid segment.

Embodiment 72

The method of embodiment 71, wherein the second transposon end includes a nucleotide sequence different from that of the first artificial transposon end.

Embodiment 73

The method of embodiment 71 or 72, wherein the second transposon end includes a second artificial transposon end including a sequence wherein at least 2 nucleotides of the corresponding wildtype transposon end sequence have each been substituted with a different nucleotide, said substitutions defining a barcode.

Embodiment 74

The method of embodiments 69-73, wherein the method includes contacting sample nucleic acids with a set of first artificial transposon ends, wherein different first artificial transposon ends have different barcodes.

Embodiment 75

The method of embodiments 73 or 74, wherein the method includes contacting sample nucleic acids with a set of second artificial transposon ends, wherein different second artificial transposon ends have different barcodes.

Embodiment 76

The method of embodiments 73-75, wherein different barcodes are employed to identify nucleic segments from different samples.

Embodiment 77

The method of embodiments 69-76, wherein the method additionally includes sequencing the tagged nucleic acid molecule using a primer that binds within the artificial transposon end and primes polymerization of a nucleotide sequence including the barcode.

Embodiment 78

The method of embodiments 69-77, wherein the barcode includes at least 3 nucleotides.

Embodiment 79

The method of embodiments 69-78, wherein the barcode nucleotides are adjacent to one another.

Embodiment 80

The method of embodiment 79, wherein the method additionally includes sequencing the tagged nucleic acid molecule using a primer that binds within the artificial transposon end at a site adjacent to the barcode and primes polymerization of a nucleotide sequence including the barcode, which is adjacent to any invariant transposon end nucleotide(s), which is/are adjacent to the sample nucleic acid segment.

BRIEF DESCRIPTION OF THE DRAWINGS

FIG. 3A-3C illustrates the use of transposon-mediated barcoding to facilitate correct calling of heterozygotes versus homozygotes. (3A) The left panel shows that DNA sequencing generates a large number of reads having the same single nucleotide polymorphism (SNP), which could indicate a homozygote for the SNP or loss of a different allele ("allele dropout"). The right panel shows that transposon-mediated barcoding generates only one barcode-nucleic acid segment combination, indicating only one transposition event on one allele; accordingly, there is a high probability of allele dropout, which means that no reliable determination can be made as to whether the sample is heterozygous or homozygous for the SNP. (3B) The left panel shows that DNA sequencing generates a large number of reads having SNP A at a locus and one read having SNP G; this could reflect a heterozygote or a sequencing error. (Note: the sequences are shown in two different colors to indicate that they originated from two different chromosomes; however, they appear identical in sequencing reads, except for the SNP.) The right panel shows that transposon-mediated barcoding generates two different barcode-nucleic acid segment combinations, indicating that the nucleic acid segment is present in two copies having different sequences for the SNP, i.e., that the sample is heterozygous for this SNP. (3C) The left panel shows that DNA sequencing generates a number of reads having SNP A at a locus and a number of reads having SNP G; this could reflect a heterozygote or a sequencing error. (As above, the sequences are shown in two different colors to indicate that they originated from two different chromosomes; however, they appear identical in sequencing reads, except for the SNP.) The right panel shows that transposon-mediated barcoding generates two different barcode-nucleic acid segment combinations (upper set and lower set of reads), indicating that the nucleic acid segment is present in two copies; because one combination (lower set of reads) has two different bases at the SNP site, it can be concluded that an amplification or sequencing error gave rise to one of these bases.

FIG. 9A-B shows alignments of sequences obtained from the study described in Example 3. (9A) Chromosomal DNA sequences; (9B) Mitochondrial DNA sequences.

FIG. 10 shows alignments of additional chromosomal DNA sequences obtained from the study described in Example 3. The consensus is represented in upper case, while non-consensus is represented in lower case. The arrows highlight the potential use of barcodes to discern true variants from possible sequencing error

DETAILED DESCRIPTION

Figure 1:
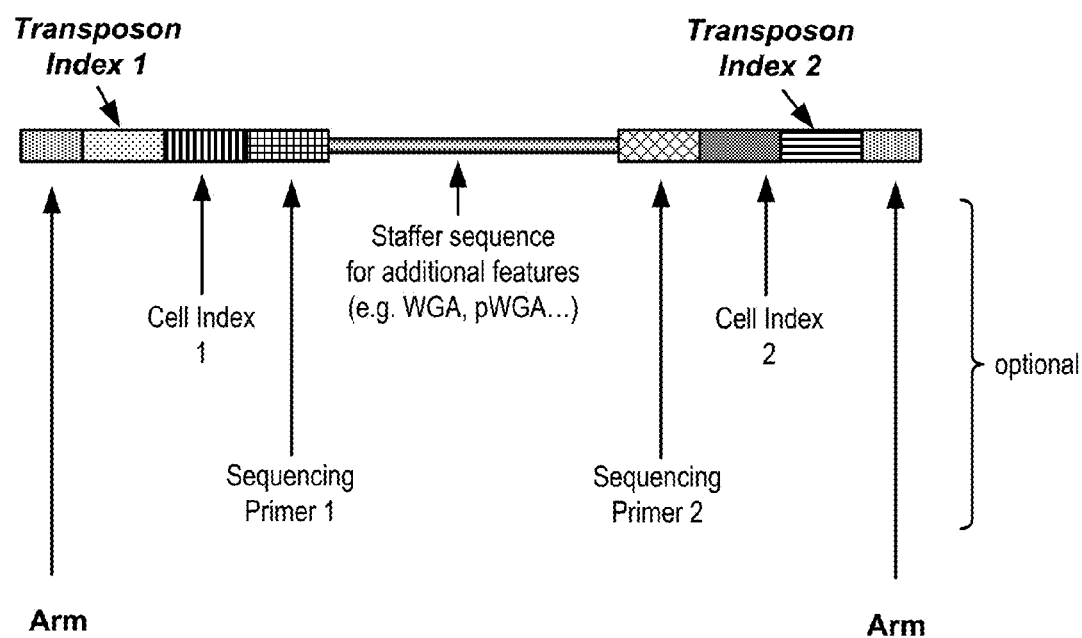
FIG. 1 shows the structure of an illustrative transposon for use in incorporating barcodes into nucleic acids according to the methods described herein.

In certain embodiments, the present invention provides a way of "digitally" marking different alleles of different chromosomes by using a transposase to insert differently barcoded transposons into genomic DNA, e.g., derived from a single cell or a defined number of identical cells, before further analysis. According to this method, each allele becomes marked with a unique pattern of transposon barcodes. Because each unique pattern of transposon barcodes identifies a particular allele, the method facilitates determinations of ploidy and copy number variation, improves the ability to discriminate among homozygotes, heterozygotes, and patterns arising from sequencing errors, and allows loci separated by uninformative stretches of DNA to be identified as linked loci, thereby facilitating haplotype determinations. Such determinations have previously been made using high-throughput DNA sequencing results, which include particular sequences, and the number of times they were detected (i.e., the number of "reads" of a particular sequence). However, these results are often difficult to interpret due to differences in amplification efficiency and sequencing errors. The method described herein overcomes these problems by making it possible to clearly identify the presence of different alleles. Thus, for example, copy number variations (CNVs) can be unambiguously identified because the number of unique transposon barcode patterns associated with a particular nucleic acid segment of interest equals the number of alleles present. This method therefore allows easy distinction between a cell that is triploid for the allele (giving rise to three unique patterns) and a cell that is diploid, but in which one allele is over-amplified during analysis (but having only two unique patterns).

Definitions

Terms used in the claims and specification are defined as set forth below unless otherwise specified.

The term "nucleic acid" refers to a nucleotide polymer, and unless otherwise limited, includes known analogs of natural nucleotides that can function in a similar manner (e.g., hybridize) to naturally occurring nucleotides.

The term nucleic acid includes any form of DNA or RNA, including, for example, genomic DNA; complementary DNA (cDNA), which is a DNA representation of mRNA, usually obtained by reverse transcription of messenger RNA (mRNA) or by amplification; DNA molecules produced synthetically or by amplification; and mRNA.

The term nucleic acid encompasses double- or triple-stranded nucleic acids, as well as single-stranded molecules. In double- or triple-stranded nucleic acids, the nucleic acid strands need not be coextensive (i.e., a double-stranded nucleic acid need not be double-stranded along the entire length of both strands).

The term nucleic acid also encompasses any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

More particularly, in certain embodiments, nucleic acids, can include polydeoxyribonucleotides (containing 2-deoxy-D-ribose), polyribonucleotides (containing D-ribose), and any other type of nucleic acid that is an N- or C-glycoside of a purine or pyrimidine base, as well as other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. The term nucleic acid also encompasses linked nucleic acids (LNAs), which are described in U.S. Pat. Nos. 6,794,499, 6,670,461, 6,262,490, and 6,770,748, which are incorporated herein by reference in their entirety for their disclosure of LNAs.

The nucleic acid(s) can be derived from a completely chemical synthesis process, such as a solid phase-mediated chemical synthesis, from a biological source, such as through isolation from any species that produces nucleic acid, or from processes that involve the manipulation of nucleic acids by molecular biology tools, such as DNA replication, PCR amplification, reverse transcription, or from a combination of those processes.

As used herein, the term "complementary" refers to the capacity for precise pairing between two nucleotides. I.e., if a nucleotide at a given position of a nucleic acid is capable of forming canonical hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. The degree of complementarity between nucleic acid strands has significant effects on the efficiency and strength of hybridization between nucleic acid strands. A first nucleotide sequence is said to be the "complement" of a second sequence if the first nucleotide sequence is complementary to the second nucleotide sequence. A first nucleotide sequence is said to be the "reverse complement" of a second sequence, if the first nucleotide sequence is complementary to a sequence that is the reverse (i.e., the order of the nucleotides is reversed) of the second sequence.

"Specific hybridization" refers to the binding of a nucleic acid to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

In particular embodiments, hybridizations are carried out under stringent hybridization conditions. The phrase "stringent hybridization conditions" generally refers to a temperature in a range from about 5° C. to about 20° C. or 25° C. below than the melting temperature ($T_m$) for a specific sequence at a defined ionic strength and pH. As used herein, the $T_m$ is the temperature at which a population of double-stranded nucleic acid molecules becomes half-dissociated into single strands. Methods for calculating the $T_m$ of nucleic acids are well known in the art (see, e.g., Berger and Kimmel (1987) METHODS IN ENZYMOLOGY, VOL. 152: GUIDE TO MOLECULAR CLONING TECHNIQUES, San Diego: Academic Press, Inc. and Sambrook et al. (1989) MOLECULAR CLONING: A LABORATORY MANUAL, 2ND ED., VOLS. 1-3, Cold Spring Harbor Laboratory), both incorporated herein by reference). As indicated by standard references, a simple estimate of the $T_m$ value may be calculated by the equation: $T_m=81.5+0.41(\% \text{ G+C})$, when a nucleic acid is in aqueous solution at 1 M NaCl (see, e.g., Anderson and Young, Quantitative Filter Hybridization in NUCLEIC ACID HYBRIDIZATION (1985)). The melting temperature of a hybrid (and thus the conditions for stringent hybridization) is affected by various factors such as the length and nature (DNA, RNA, base composition) of the primer or probe and nature of the target nucleic acid (DNA, RNA, base composition, present in solution or immobilized, and the like), as well as the concentration of salts and other components (e.g., the presence or absence of formamide, dextran sulfate, polyethylene glycol). The effects of these factors are well known and are discussed in standard references in the art. Illustrative stringent conditions suitable for achieving specific hybridization of most sequences are: a temperature of at least about 60° C. and a salt concentration of about 0.2 molar at pH7.

The term "oligonucleotide" is used to refer to a nucleic acid that is relatively short, generally shorter than 200 nucleotides, more particularly, shorter than 100 nucleotides, most particularly, shorter than 50 nucleotides. Oligonucleotides may be single-stranded or double-stranded DNA molecules.

The term "primer" refers to an oligonucleotide that is capable of hybridizing (also termed "annealing") with a nucleic acid and serving as an initiation site for nucleotide (RNA or DNA) polymerization under appropriate conditions (i.e., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but primers are typically at least 7 nucleotides long and, more typically range from 10 to 30 nucleotides, or even more typically from 15 to 30 nucleotides, in length. Other primers can be somewhat longer, e.g., 30 to 50 nucleotides long. In this context, "primer length" refers to the portion of an oligonucleotide or nucleic acid that hybridizes to a complementary target sequence and primes nucleotide synthesis. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the template to which a primer hybridizes.

A primer is said to anneal to another nucleic acid if the primer, or a portion thereof, hybridizes to a nucleotide sequence within the nucleic acid. The statement that a primer hybridizes to a particular nucleotide sequence is not intended to imply that the primer hybridizes either completely or exclusively to that nucleotide sequence.

The primer can be perfectly complementary to the target nucleic acid sequence or can be less than perfectly complementary. In certain embodiments, the primer has at least 65% identity to the complement of the target nucleic acid sequence over a sequence of at least 7 nucleotides, more typically over a sequence in the range of 10-30 nucleotides, and often over a sequence of at least 14-25 nucleotides, and more often has at least 75% identity, at least 85% identity, at least 90% identity, or at least 95%, 96%, 97%. 98%, or 99% identity. It will be understood that certain bases (e.g., the 3' base of a primer) are generally desirably perfectly complementary to corresponding bases of the target nucleic acid sequence. Primer and probes typically anneal to the target sequence under stringent hybridization conditions.

The term "transposon" refers to a nucleic acid molecule that is capable of being incorporated in to a nucleic acid by a transposase enzyme. A transposon includes two transposon ends (also termed "arms") linked by a sequence that is sufficiently long to form a loop in the presence of a transposase. Transposons can be double-, single-stranded, or mixed, containing single- and double-stranded region(s), depending on the transposase used to insert the transposon. For Mu, Tn3, Tn5, Tn7 or Tn10 transposases, the transposon ends are double-stranded, but the linking sequence need not be double-stranded. In a transposition event, these transposons are inserted into double-stranded DNA.

The term "transposon end" refers to the sequence region that interacts with transposase. The transposon ends are double-stranded for transposases Mu, Tn3, Tn5, Tn7, Tn10 etc. The transposon ends are single-stranded for transposases IS200/IS605 and ISrad2, but form a secondary structure, just like a double-stranded region. In a transposition event, single-stranded transposons are inserted into single-stranded DNA by a transposase enzyme.

The term "artificial transposon end" refers to a transposon end in which one or more positions in a wildtype transposon end have been substituted with one or more different nucleotides.

The term "transposase" refers to an enzyme that binds to transposon ends and catalyzes their linkage to other double- or single-stranded nucleic acids, such as genomic DNA. Transposases usually comprise an even-number of subunits and bind two transposon ends. The two transposon ends can be of identical sequence or of different sequences.

As used herein, the terms "barcode sequence" and "index sequence" are used to refer to nucleotide sequences that encode information. For example, a "transposon barcode sequence" can identify a particular transposon. An "index sequence" can identify, e.g., the source of the sample nucleic acids under analysis, such as nucleic acids from a particular sample or a particular reaction. Barcodes can be used to distinguish different cells, different treatments, different time points, different positions in space, etc.

"UMI" is an acronym for "unique molecular index," also referred to as "molecular index." A UMI is one in a group of indexes in which each index (or barcode) has an index sequence that is different from any of the other indexes in the group. One way to achieve this "uniqueness" is to use a string of nucleotides. For example, if the length of this string is 10 bases, there are more than 1 million unique sequences; if it is 20 bases long, there will be $10^{12}$ unique sequences.

The term "adjacent," when used herein to refer two nucleotide sequences in a nucleic acid, can refer to nucleotide sequences separated by 0 to about 20 nucleotides, more specifically, in a range of about 1 to about 10 nucleotides, even more specifically, in a range of about 1 to about 5 nucleotides or to sequences that directly abut one another.

The term "inside" when used herein to refer to the position of nucleotide sequences within a transposon denotes a position closer to the center of the transposon. Thus, a primer binding site is said to be inside of a barcode sequence if it is closer to the center of the transposon than the barcode sequence.

As used herein, the term "associated with" is used herein to describe nucleic acid elements (e.g., barcodes, transposons, etc.) that are physically linked to nucleic acid sequences of interest and in sufficiently close proximity to be detected together by methods such as amplification and DNA sequencing. A barcode that is associated with a gene or other nucleic acid segment is incorporated into and physically linked to that gene or segment. The barcode can be inserted into the gene or segment or appended to an end of the gene or segment. A barcode that is associated with a single nucleotide polymorphism (SNP) is physically linked to that SNP.

"Amplification" according to the present teachings encompasses any means by which at least a part of at least one target nucleic acid is reproduced, typically in a template-dependent manner, including without limitation, a broad range of techniques for amplifying nucleic acid sequences, either linearly or exponentially. Illustrative means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. Nos. 6,027,998; 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html-); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18-(2002); Lage et al., Genome Res. 2003 February; 13(2):294-307, and Landegren et al., Science 241:1077-80 (1988), Demidov, V., Expert Rev Mol Diagn. 2002 November; 2(6):542-8., Cook et al., J Microbiol Methods. 2003 May; 53(2):165-74, Schweitzer et al., Curr Opin Biotechnol. 2001 February; 12(1):21-7, U.S. Pat. Nos. 5,830,711, 6,027,889, 5,686,243, PCT Publication No. WO0056927A3, and PCT Publication No. WO9803673A1.

In some embodiments, amplification comprises at least one cycle of the sequential procedures of: annealing at least one primer with complementary or substantially complementary sequences in at least one target nucleic acid; synthesizing at least one strand of nucleotides in a template-dependent manner using a polymerase; and denaturing the newly-formed nucleic acid duplex to separate the strands. The cycle may or may not be repeated. Amplification can comprise thermocycling or can be performed isothermally.

"Whole genome amplification" ("WGA") refers to any amplification method that aims to produce an amplification product that is representative of the genome from which it was amplified. Illustrative WGA method include Primer extension PCR (PEP) and improved PEP (I-PEP), Degenerated oligonucleotide primed PCR (DOP-PCR), Ligation-mediated PCR (LMP), T7-based linear amplification of DNA (TLAD), Multiple displacement amplification (MDA).

The term "amplification-based detection" refers to any detection method in which a nucleic acid sequence of interest can be detected solely by detecting the presence of an amplicon, usually using by detecting a dye or label, without the need to analyze the size or sequence of the amplicon.

The term "qPCR" is used herein to refer to quantitative real-time polymerase chain reaction (PCR), which is also known as "real-time PCR" or "kinetic polymerase chain reaction."

As used herein with respect to determining genome-wide copy number variation, the resolution of the analysis is expressed in terms of the average distance between loci whose copy number are determined. Accordingly, a "less than X kilobase resolution, on average" means that copy numbers are determined for loci throughout the genome that are separated by an average distance of less than X kilobases.

When used with reference to a cell, the term "diploid" refers to having two sets of unpaired chromosomes. When used with reference to a genetic locus or segment, the term "diploid" refers to the presence of that locus or segment in two copies.

When used with reference to a cell, the term "haploid" refers to having a single set of unpaired chromosomes. When used with reference to a genetic locus or segment, the term "haploid" refers to the presence of that locus or segment in one copy only.

An organism or cell may have one or more chromosomes in excess of the haploid number or of an exact multiple of the haploid number characteristic of the species. The result is one or more unbalanced sets of chromosomes, which are referred to as "hyperdiploid," "hyperdiploid," "hypertetraploid," and so on, depending on the number of multiples of the haploid number they contain.

An organism or cell may have fewer than the haploid number or than an exact multiple of the haploid number of chromosomes characteristic of the species. These one or more unbalanced sets of chromosomes are referred to as "hypodiploid," "hypotriploid," "hypotetraploid," and so on, depending on the number of multiples of the haploid chromosomes they contain.

"Trisomy," an example of hyperploidity, is a condition of having three copies of a given chromosome or chromosome segment in each somatic cell rather than the normal number of two.

Any deviation from an exact multiple of the haploid number of chromosomes, whether fewer or more, is termed "aneuploidy." Aneuploidy is consistently observed in virtually all cancers. Somatic mosaicism occurs in virtually all cancer cells, including trisomy 12 in chronic lymphocytic leukemia (CLL) and trisomy 8 in acute myeloid leukemia (AML). Aneuploid cancer cells may have hypoploidy for some chromosomes, while hyperploidy for others.

As used herein, the term "haplotype" refers to a combination of loci at adjacent locations on a chromosome that are physically linked together through deoxyribonucleic acid backbone. A translocation or chromothripsis generate new haplotypes that did not exist before the event.

As use herein, the term "variation" is used to refer to any difference. A variation can refer to a difference between individuals or populations. A variation encompasses a difference from a common or normal situation. Thus, a "copy number variation" or "mutation" can refer to a difference from a common or normal copy number or nucleotide sequence. Other types of variation include those arising from changes in chromosome structure, as in the case of translocation or chromothrepsis and the combination of both. An "expression level variation" or "splice variant" can refer to an expression level or RNA or protein that differs from the common or normal expression level or RNA or protein for a particular, cell or tissue, developmental stage, condition, etc.

"Haploidome" refers to the complete genetic information within a cell that includes the information on haplotypes, SNPs, and copy number variation (including chromosome number variation). For a gene with a copy number variation, a haploidome determination can provide not only have the information on the number of the copy, but also the information on the location, orientation, and neighboring genes of a variant copy. It has been reported that a single cell may contain 4, 6, 8, or up to hundreds' of full sets of chromosomes. These cells have uniformly changed copy numbers throughout the genome. Haploidomes of these single cells capture the number change information.

Tumor cells in tumor tissues or in established tumor cell lines tend to be even more complex and heterogeneous. A complete haploidome determination provides the full description of the genetic information down to the single nucleotide level.

"Chromothripsis" refers to the phenomenon by which up to thousands of clustered chromosomal rearrangements occur in a single event in localized and confined genomic regions in one or a few chromosomes, and which is known to be involved in both cancer and congenital diseases.

A "polymorphic marker" or "polymorphic site" is a locus at which nucleotide sequence divergence occurs. Illustrative markers have at least two alleles, each occurring at frequency of greater than 1%, and more typically greater than 10% or 20% of a selected human population. A polymorphic site may be as small as one base pair. Polymorphic markers include restriction fragment length polymorphism (RFLPs), variable number of tandem repeats (VNTR's), hypervariable regions, minisatellites, dinucleotide repeats, trinucleotide repeats, tetranucleotide repeats, simple sequence repeats, deletions, and insertion elements such as Alu. The first identified allelic form is arbitrarily designated as the reference form and other allelic forms are designated as alternative or variant alleles. The allelic form occurring most frequently in a selected population is sometimes referred to as the "wildtype" form or as the "major allele." The allelic form occurring least frequently in a selected population may be referred to as the "minor allele." It should be emphasized that "major allele" and "minor allele" are terms used in population genetics; these terms are not typically used to describe alleles in single cells absent information about the alleles in the larger population. The term "mutant allele" is used to describe an allelic form that differs from the major allele and, in some cases, encode a protein having altered function. Diploid organisms may be homozygous (i.e, diploid) or heterozygous for allelic forms. A diallelic polymorphism has two forms. A triallelic polymorphism has three forms.

A "single nucleotide polymorphism" (SNP) occurs at a polymorphic site occupied by a single nucleotide, which is the site of variation between allelic sequences. The site is usually preceded by and followed by highly conserved sequences of the allele (e.g., sequences that vary in less than $1/100$ or $1/1000$ members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele.

A "single nucleotide variation" (SNV) refers to a single nucleotide difference, relative to a standard reference sequence, at a site that is not a typical site of variation between allelic sequences. An SNV reflects an individual mutation, rather than an allelic difference.

As used herein, the term "identical cells" refers to a set of cells that are clones of one another. As such, any genetic variation is expected to be sufficiently small that the methods described below produce barcode patterns that are interpretable in essentially the same manner as when a single cell is analyzed.

A "structural gene" is a gene that encodes any RNA or protein product other than a regulatory factor (i.e., regulatory protein).

A "regulatory gene" is a gene involved in controlling the expression of one or more other genes. A regulatory gene may encode a protein, or it may work at the level of RNA, as in the case of genes encoding microRNAs.

Methods of Using Transposon Barcodes for Marking Nucleic Acids

In General

In certain embodiments, the invention provides a method for marking sample nucleic acids to identify alleles, thereby facilitating a variety of determinations, including linkage determinations, and enhancing the ability to correctly identify copy number variations (CNVs), single nucleotide polymorphisms (SNPs), single nucleotide variations (SNVs), and sequencing errors. The method entails contacting the sample nucleic acids with a loaded transposase capable incorporating transposons into the sample nucleic acids. The contacting is carried out under conditions suitable for incorporation of the transposons into the sample nucleic acids, thereby forming nucleic acid molecules, wherein particular transposon barcodes are associated with particular nucleic acid segments. For any locus of interest, the number of different transposon-nucleic acid segment combinations is detected and gives the number of alleles in the sample nucleic acids for that locus. Depending on the transposons employed, the method will give rise to different types of transposon-nucleic acid segment combinations.

For example, if the transposons employed are all identical, different combinations can be distinguished based on insertion site. In particular, the transposon insertion site is essentially random (at least in purified DNA). Therefore, an insertion density of one insertion event per average about 300 base to about 1 Kb means that within the about 300 base to about 1 Kb range, there are about 300 to about 1000 possible sites into which a transposon can insert. In another words, the chance that two insertions happen at the same site is one in about 300 to about 1000. These odds are generally good enough to distinguish two alleles from a normal cell. If the region is expanded to 10 Kb, then the combination of multiple insertion events will increase the resolution of the analysis. For identical transposons, then, possible different transposon-nucleic acid segment combinations include: (1) nucleic acid segments with no transposons, (2) nucleic acid segments with at least one transposon in different insertion sites, and (3) nucleic acid segments with different numbers of transposons, and combinations thereof. Most structural genes have sufficient sequence complexity that every insertion site is unique. In this case, each pattern observed arises from one allele present in the sample nucleic acids. However, this particular method will not work as well for regions that are highly repetitive. For such regions, one of the methods described below (e.g., the use of barcoded transposons) is preferred.

In certain embodiments, non-identical transposons can be employed. For example, different transposons having different end sequences are known and available for use in in vitro transposition reactions. Different wildtype transposon end sequences, such as those from Tn3, Tn5, Tn10, or mu, can serve as "barcodes" for marking alleles. The use of such transposons in the methods described herein gives rise to another possible different transposon-nucleic acid segment combination, namely, nucleic acid segments with different transposon end sequences, or combinations thereof, which may be found in different insertion sites.

In addition to wildtype transposons that differ from one another, non-identical transposons include transposons that have been engineered to have different sequences. Different nucleotides or sequences can be incorporated into a stuffer sequence between the transposon end sequences required for binding to the corresponding transposase. As shown in FIG. 1, any desired barcodes/indexes can be engineered into any region other than the transposon end. Alternatively, or in addition, different nucleotides or sequences can be incorporated into non-critical base(s) of the transposon ends. The possibilities for barcodes incorporated into the transposon end are more constrained, depending on the sequence requirements for binding to the transposase. In some embodiments, multiple transposons, each having a different barcode sequence, are used to form barcoded nucleic acid molecules, wherein particular transposon barcodes are associated with particular nucleic acid segments. In this case, the number of different barcode-nucleic acid segment combinations can be detected for any locus of interest and gives the number of alleles at that locus.

Any of the above-discussed approaches can be used in combination. For example, in most embodiments, different combinations will be distinguished, at least in part, based on different insertion sites. In addition, in some embodiments, it may be advantageous to use barcoded transposons of several different types (e.g., Tn3, Tn5, Tn10, or mu). For example, one might use 10 barcoded transposons with Tn3 ends to barcode DNA accessible in chromatin, followed purification of the DNA and a second round of transposition using 10 barcoded transopons with mu ends. Tn3-marked sequences would indicate chromatin in an "open" configuration (described further below), which is associated with transcription (euchromatin). Detection of Tn3/barcoding patterns would allow identification of alleles in transcribed regions of the genome; whereas, detection of mu/barcoding patterns would allow identification of alleles in non-transcribed regions.

For ease of discussion, the method is described in terms of the use of transposons comprising barcodes. However, those of skill in the art will readily appreciate that the considerations discussed below apply equally to non-barcoded transposons.

In certain embodiments, e.g., where genome-wide analysis is desired, whole genome amplification of the barcoded nucleic acid molecules can be carried out to produce nucleic acids for identification of different barcode-nucleic acid segment combinations. In other embodiments, one or more particular genomic regions of interest can be amplified for further analysis as described herein. In either case, amplification of the barcoded nucleic acid molecules can be carried out to produce amplicons that each includes a combination of one or more barcode(s) and one or more associated nucleic acid segments. The amplicons are detected by any method that permits a determination of the barcode-nucleic acid segment combination(s), i.e., the pattern of barcodes associated with a given nucleic acid segment. This analysis can be carried out by any convenient method, such as, DNA sequencing.

In some embodiments, the method is employed to barcode genomic DNA, which can be obtained from one or a small defined number of cells. In various embodiments, the number of cells can be 1, or 2, 3, 4, 5, 6, 7, 8, 9, or 10, e.g., if they are identical, or can fall within a range bounded by any of these values, e.g., 1-5, 1-4, 1-3, and 1-2. Generally, the smaller the number of cells used for the sample nucleic acids, the simpler the interpretation of the barcode-nucleic acid segment combination(s). Accordingly, sample nucleic acids derived from a single cell are preferably employed as the sample nucleic acids in this method.

An illustrative workflow for this method can entail: (1) isolating DNA from a single cell, (2) introducing transposon barcodes into genomic DNA, (3) whole genome amplification, and (4) next-generation sequencing (NGS).

The method can be employed to incorporate any desired number of different barcodes into the sample nucleic acids. In various embodiments, the method entails incorporating 1, 2, 3, 4, 5, 6, 7, 8, 9, 10, 15, 20, 25, 30, 35 40, 45, or 50 or more different barcodes into the sample nucleic acids. In some embodiments, the number of barcodes incorporated can fall within a range bounded by any of these values, e.g., 5-25 or 10-15.

By adjusting the conditions, such as the relative concentrations of transposons, transposase, and sample nucleic acids, the frequency of transposon incorporation can be adjusted to produce the desired barcode density. In various embodiments, one transposon is incorporated, on average, every 100, 200, 300, 400, 500, 600, 700, 800, 900 basepairs (bp) or 1, 1.5, 2, 2.5, 3, 3.5, 4, 4.5, 5, 5.5, 6, 6.5, 7, 7.5, 8, 8.5, 9, 9.5, or 10 kilobases (Kb) or more. In some embodiments, the average frequency of transposon incorporation can fall within any range bounded by any of these values, e.g, every 200 bp to 10 Kb, every 500 bp to 5 Kb, or every 500 bp to 1.5 Kb. In a genome-wide analysis, the frequency of transposon incorporation, i.e., the barcode density, determines the resolution of the analysis. Thus, a barcode density of one barcode every 500 bases provides a 500-base resolution, which means that copy number differences in genomic segments of approximately this size can readily be identified, even in the absence of any prior information (e.g., sequence information) about the segment. By adjusting the barcode density, therefore, virtually any desired degree of resolution can be achieved, e.g., about: 100, 200, 300, 400, 500, 600, 700, 800, 900 bp or 1, 1.5, 2, 2.5, 3, 3.5, 4, 4.5, 5, 5.5, 6, 6.5, 7, 7.5, 8, 8.5, 9, 9.5, or 10 Kb resolution. In various embodiments, the degree of resolution of a genome-wide analysis can fall within any range bounded by any of these values, e.g., 200 bp to 10 Kb, 500 bp to 5 Kb, or 500 bp to 1.5 Kb.

The frequency of transposon incorporation will vary, depending upon the transposase employed, and those of skill in the art can empirically determine suitable conditions, including relative concentrations of transposons and sample nucleic acids to achieve the desired barcode density.

In some embodiments, transposon incorporation is essentially random, e.g., when the sample nucleic acids are purified to remove histone proteins and other components that could block transposition. In other embodiments, transposon incorporation can be targeted certain regions of DNA, depending on their function or state. In one embodiment, for example, when cells are lysed gently, without disruption of histone binding, only open chromatin regions are exposed to transposition. In another illustrative embodiment, transposition can be preferentially excluded from CpG islands, if the sample nucleic acids are allowed to interact with methyl-CpG-binding domain (MBD) proteins before transposition.

Applications

Transposon-mediated barcoding may be used in any application in which the resultant transposon barcodes can be exploited in further analysis of the barcoded nucleic acid molecules. For a variety of genome-wide analyses, conditions are adjusted so that it is extremely unlikely that the same pattern of barcodes will appear in any two alleles. For example, ten different transposon barcodes (e.g., BC1, BC2, BC3, . . . BC10) can be employed in a reaction that inserts one transposon, on average, every 1000 bp. A 10 Kb region will, on average, contain ten transposons, with $10^{10}$ possible permutations in arrangement of transposons in this region. The insertion sites are substantially random because, although hot spots exist, they will be "filled in" by transposons during transposition, leaving the remaining transposons free to insert randomly. Assuming substantially random insertion, the total possible number of patterns of transposon barcodes is enormous, ensuring that the odds of two alleles for this region having the same barcodes incorporated into the same sites are vanishingly small. As long as this is true, the number of different barcode-nucleic acid segment combinations that include all or a portion of a locus of interest can be detected to determine the copy number of that locus. The detection of one such combination indicates that the locus is either haploid (e.g., a locus on the Y chromosome) or possible that allele-dropout has occurred in the course of the analysis. The detection of two such different combinations indicates that the locus is diploid. A number of types of differences are commonly observed in the case of a diploid locus.

First, a nucleic acid segment may be detected in two forms, each characterized by different a barcode(s). For example, a particular nucleic acid segment may be covered 5 times in a following fashion in NGS reads ("Ref" is the non-barcoded sequence for this segment):

```
Ref:
                                              (SEQ ID NO: 1)
A T C G G T A T C G A A A T C C G T C C C G G T

Read1:
                                              (SEQ ID NO: 2)
      G T A T C GxA A A T C C G T C C C G G T Read2:
                                              (SEQ ID NO: 3)
  T C G G T A T C GxA A A T C C G T C C C C Read3:
                                              (SEQ ID NO: 4)
      G G T A T C GyA A A T C C G T C C C C Read4:
                                              (SEQ ID NO: 5)
  T C G G T A T C GyA A A T C C G T C C C C G Read5:
                                              (SEQ ID NO: 6)
              T C GyA A A T C C G T C C C C G
```

Here, x and y refer to two different barcode sequences. If x and y are 10 bases long, then the chance that read 1 and 2 derive from two separate transposition events is one in a million. Similarly, the chance that read 3 and 4, read 3 and 5, and read 4 and 5 derive from separate transposition events is one in a million. As reads 1 and 2, on the one hand, and reads 3-5, on the other, clearly reflect two different transposition events, it can be determined that this single cell has two copies of this segment (but not more than two copies).

Second, a nucleic acid segment may have only one barcode, but it may be found in two different locations in the segment. For example, if five reads obtained are as follows:

```
Ref:
                                              (SEQ ID NO: 7)
A T C G G T A T C G A A A T C C G T C C C G G T

Read1:
                                              (SEQ ID NO: 8)
      G T A T C GxA A A T C C G T C C C G G T Read2:
                                              (SEQ ID NO: 9)
  T C G G T A T C GxA A A T C C G T C C C C Read3:
                                              (SEQ ID NO: 10)
      G G T A T C G A A A T C C GxT C C C C Read4:
                                              (SEQ ID NO: 11)
  T C G G T A T C G A A A T C C GxT C C C C G Read5:
                                              (SEQ ID NO: 12)
              T C G A A A T C C GxT C C C C G
```

Since the transposon with identical barcode x incorporates into two different positions, it can be concluded that reads 1 and 2, on the one hand, and reads 3-5, on the other, must come from two separate events. Accordingly, the cell has two copies of this segment (but not more than two copies).

Third, a nucleic acid segment may be detected in two forms: one associated with a barcode(s) and one not containing any barcode. An example is shown below:

```
Ref:
                                              (SEQ ID NO: 13)
A T C G G T A T C G A A A T C C G T C C C G G T

Read1:
                                              (SEQ ID NO: 14)
      G T A T C GxA A A T C C G T C C C G G T Read2:
                                              (SEQ ID NO: 15)
  T C G G T A T C GxA A A T C C G T C C C C
```

-continued

Read3:
(SEQ ID NO: 16)
G G T A T C G A A A T C C G T C C C C

Read4:
(SEQ ID NO: 17)
T C G G T A T C G A A A T C C G T C C C G

Read5:
(SEQ ID NO: 18)
T C G A A A T C C G T C C C G

The presence of barcode x in the same position in reads 1 and 2 indicates that these reads derive from one transposition event in a first copy of this segment, whereas the absence of a barcode in read 3-5 indicates the presence of a second segment in which no transposition occurred. Accordingly, the cell has two copies of this segment (but not more than two copies).

Although most normal somatic mammalian cells are diploid, consisting of 22 pairs of autosome and two sex chromosomes, some normal cells exist in multiploid forms. For example, cardiomyocytes are typically tetraploid, as are hapatocytes, while trophoblast cells in embryos have 1000 sets of chromosomes. In addition, some cancer cells have varying numbers of chromosomes, from less than 46 to more than 92. HeLa cells from one cell line at one time point, for example, have a total of 76 to 82 chromosomes. Among them, one cell has six copies of chromosome 5 and five copies chromosome 9 in a karyotyping study. Such cells are also characterized by lot of chromosomal translocation leading to mosaic structure. Other phenomena have been reported that lead to more than two sets of chromosomes in a single cell. For example, cell-in-cell formation arises from entosis. The methods described here can be used in characterizing all such deviations from the typical diploid situation.

In some embodiments, transposon-mediated barcoding is employed to identify one or more gains in copy number. More specifically, when the detected number of barcode-nucleic acid segment combinations is greater than the expected normal number of alleles for the locus, the sample is identified as one wherein the locus is at a higher than expected copy number in the cell. Multiple loci can be analyzed to distinguish between the gain of a particular locus, chromosomal sub-region, chromosome arm, or entire chromosome and a cell that has altered ploidy, e.g., a cell that is tetraploid, rather than diploid. For example, a high-resolution genome-wide analysis can be used to identify small gains throughout the genome, whereas low-resolution genome-wide analysis can be used to identify larger gains, e.g., of chromosome arms or entire chromosomes.

Copy number losses cannot generally be definitively identified by this method alone because the method cannot distinguish between the case of an allele that was not present in the starting sample nucleic acids (e.g., nucleic acids derived from a single cell) and an allele that dropped out during amplification. Therefore, when the detected number of barcode-nucleic acid segment combinations is less than the expected normal number of alleles for the locus, the sample is identified as one wherein either the locus is at a lower than expected copy number in the cell or allele-dropout may have occurred during amplification. In this case, further analysis may be done in an effort to distinguish these two possibilities, such as repeating the analysis or using a different method to detect the barcode-nucleic acid segment combinations.

In some embodiments, transposon-mediated barcoding is employed to identify homozygosity or heterozygosity of one or more loci. More specifically, when the detected barcode-nucleic acid segment combinations include two different combinations wherein a nucleic acid segment including the same nucleic acid sequence at the locus is associated with different barcodes, the sample is identified as diploid and homozygous for the locus. If, on the contrary, when the detected barcode-nucleic acid segment combinations include two different barcode-nucleic acid segment combinations wherein nucleic acid segments including different nucleic acid sequences at the locus are each associated with different barcodes, the sample is identified as diploid and heterozygous for the locus. Notably, true heterozygosity is readily distinguished from a sequence difference arising from a sequencing error using the methods described herein. In particular, a sequencing error gives rise to two different barcode-nucleic acid segment combinations wherein when nucleic acid segments including different nucleic acid sequences at the locus are each associated with the same barcodes, the sample is identified as one in which an error may have been introduced into the sample nucleic acid sequence during amplification or sequencing. The reason for this is that, under appropriate conditions (see above), each set of barcodes identifies a single allele, which means that any sequence difference in the associated nucleic acid segments represent an artifact of the analysis.

Figure 4:
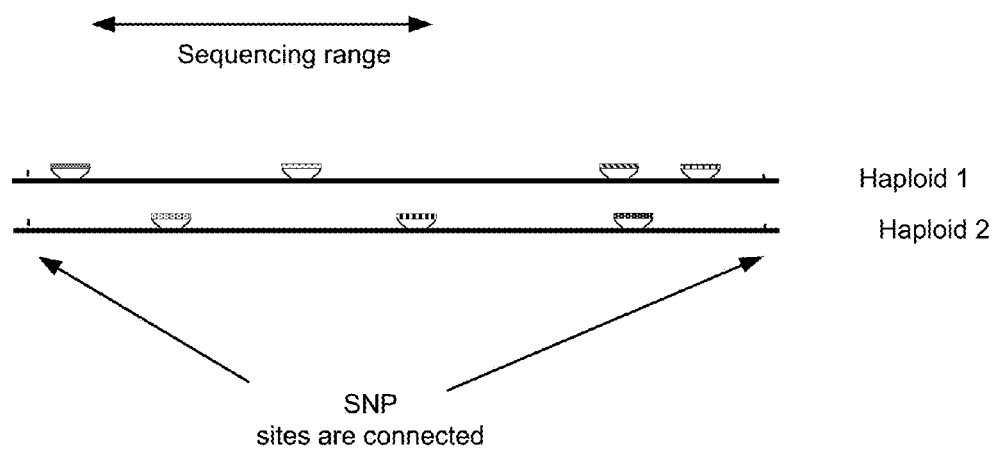
FIG. 4 illustrates the use of transposon-mediated barcoding to determine that two widely separated features (SNPs in this case) are on the same chromosome. More specifically, transposon barcodes are introduced between the SNPs, and a determination that each SNP is associated with one or more of these intervening barcode indicates that the two SNPs are linked.

In other embodiments, transposon-mediated barcoding is used to determine whether two loci that are separated from one another are actually linked, i.e., present on the same chromosome. This is particularly useful in the case of two loci that are separated by uninformative stretches of DNA that are identical in the chromosomes on which they are located. In this case, transposon-mediated barcoding can be carried out to incorporate one or more transposons into intervening sample nucleic acid sequences to produce a transposon-nucleic acid segment combination. By analyzing the loci to determine whether both loci are linked with the same a transposon-nucleic acid segment combination, one can determine whether the loci are on the same chromosome. For example, as shown in FIG. 4, transposon-mediated barcoding can carried out so that multiple barcodes are introduced into the intervening sequence, most conveniently, over a range that permits detection of plurality of barcodes, together with one of the SNPs in on sequencing run. The conditions are such that different sets of barcodes are introduced into the intervening sequence on each chromosome. Thus, for example, a determination that each of the SNPs is linked with the three barcodes shown in FIG. 4 that correspond to "Haploid 2", rather than any of the four barcodes that correspond to "Haploid 1." As suggested in FIG. 4, the initial determination might be that the left-most SNP is associated with the first and second barcodes (reading left to right) and that the right-most SNP is associated with the second and third barcodes. The presence of the common second barcode, which is associated with each of the SNPs, leads to the conclusion that the SNPs are present on the same chromosome and therefore part of the same haplotype. In practice, more complex barcode patterns are envisioned. If necessary, multiple sequencing runs throughout the intervening sequence can provide sequence information that can be assembled to span the intervening sequence, and order the barcodes in this region. Thus, there is no requirement that the initial analysis yield SNP-barcode combination with at least one common barcode, as suggested by FIG. 4.

An advantage of this approach is that it is possible determine the specific haplotype of a segment of genomic DNA containing both loci, as well as the number of copies of the segment. The latter information is obtained, in some embodiments, simultaneously with determination of linkage and haplotype by counting the number of different transposon-nucleic acid segment combinations that are linked to both loci. Thus, for example, if the analysis indicates that SNP1 and SNP2 are both linked the same transposon-nucleic acid segment combinations, but that there are three different such combination, one can has determined the haplotype at SNP1 and SNP2 for each of the three copies of the segment of DNA that are present in the sample nucleic acids.

Transposons

Transposons useful in methods such as those described here include, in addition to a first transposon barcode sequence, transposon ends flanking a stuffer sequence. The transposon optionally includes a first primer binding site. Aside from these elements, the only real constraint on transposon structure is that the transposon must be capable of being inserted into double- or single-stranded nucleic acids by a suitable transposase. In particular embodiments, the methods described herein employ sets of transposons, wherein different transposons have different barcode sequences, but the same first primer binding site, which may be located in the stuffer sequence or within a transposon end. These sets can be provided in a kit for carrying out any of the methods described herein.

In some embodiments, the first transposon barcode sequence is located in the stuffer sequence, e.g., adjacent to the transposon end. In some embodiments, the first transposon barcode sequence is located within one of the transposon ends, as described in more detail below. If desired, each transposon can include a second transposon barcode sequence, which can be the same as, or different from, the first transposon barcode sequence. The second transposon barcode sequence can be located in the stuffer sequence, e.g., adjacent to the transposon end or located within one of the transposon ends. For example, the second transposon barcode sequence can be located within or adjacent to a transposon end, with the first transposon barcode sequence is located within or adjacent to the other transposon end. See, e.g., FIG. 1.

Transposon barcode sequences will have a length sufficient to encode the desired number of different barcodes. For example, if the barcode sequence includes three nucleotides, the number of possible different barcodes is $4^3=64$. Illustrative barcode sequence lengths are: 2, 3, 4, 5, 6, 7, 8, 9, 10, 11, 12, 13, 14, 15, 16, 17, 18, 19, 20, 25, 30 35, 40, 45, 50 nucleotides or more, and can fall within any range bounded by any of these values, e.g., 10-15 nucleotides. Barcode sequences can, but need not, be contiguous. Thus, for example, a barcode sequence may be characterized by two adjacent nucleotides, with a third nucleotide separated by a few intervening non-barcode nucleotides. Non-contiguous barcode sequence can, for example, be used for barcodes located within transposon ends (see below).

In particular embodiments, it may be advantageous to include one or more other types of barcodes/index sequences in the transposon. Such other sequences are termed "index sequences" herein, simply to distinguish them from the transposon barcode sequences discussed herein. Index sequences can be used, for example, to encode any desired kind of information regarding the barcoded nucleic acid molecules, such as the cell or cells or the reaction, from which the barcoded nucleic acid molecules were derived. If desired, each transposon can include a second index sequence, which can be the same as, or different from, the first index sequence. For example, one index sequence could be used to identify the cell from which the nucleic acids were derived, and the other could be used to identify a particular reaction to which they were subjected (e.g., a particular type of WGA). In an illustrative embodiment, pictured in FIG. 1, a transposon can include a first transposon barcode sequence located within or adjacent to one transposon end, and a second transposon barcode sequence located within or adjacent to the other transposon end, wherein the first index sequence is adjacent to the first barcode sequence, and the second index sequence is adjacent to the second barcode sequence.

The statements above regarding barcodes also apply to index sequences, which can be located in the stuffer sequence, e.g., adjacent to the transposon end or located within one of the transposon ends. In certain embodiments, a first index sequence is close enough to the first barcode sequence to ensure that both sequences will be included in one sequencing read. For example, one of these sequences can be located in the transposon end and one in the stuffer sequence adjacent thereto, or both sequences can be located in the transposon end or in the stuffer sequence, and/or the index sequence can be immediately adjacent to the barcode sequence. Index sequences can be any suitable length and contiguous or non-contiguous. Illustrative barcode sequence lengths are: 2, 3, 4, 5, 6, 7, 8, 9, 10, 11, 12, 13, 14, 15, 16, 17, 18, 19, 20, 25, 30 35, 40, 45, 50 nucleotides or more, and can fall within any range bounded by any of these values, e.g., 10-15 nucleotides.

Sets of transposons useful, e.g., in analyzing nucleic acids from multiple separate cells can be provided in a kit (see below). Such a kit can include two or more sets transposons, one for each cell to be analyzed. Each transposon within a set includes a different first transposon barcode sequence, and each set of transposons is characterized by a different index sequence, which be used to identify the cell under analysis.

The first primer binding site can be any nucleotide sequence to which a primer can anneal for the purpose of priming nucleotide polymerization. The first primer binding site can be located in the stuffer sequence, e.g., adjacent to the transposon end or located within one of the transposon ends. The length of the primer binding site typically ranges from about 6 to about 50 nucleotides or more, e.g, about: 6, 7, 8, 9, 10, 11, 12, 13, 14, 15, 16, 17, 18, 19, 20, 25, 30 35, 40, 45, or 50 nucleotides, or any range defined by any of these values, e.g., 10-30 or 15-25 nucleotides. In particular embodiments, the first primer binding site is used for priming WGA. Notably, each transposon need only have one such WGA primer site because transposition can be carried out so as to incorporate transposons, on average, so that they are close enough (e.g., about 500 bp to 300 Kb) to permit priming in adjacent transposons to amplify the intervening regions of the sample nucleic acids (e.g., genomic DNA). A first primer binding site that is suitable for WGA will, in some embodiments, have a sequence that is either not found or present at low copy number in the sample nucleic acids so that priming occurs primarily at the first primer binding site.

To facilitate analysis of the barcoded nucleic acids produced upon transposition, optionally followed by WGA, one or more additional primer binding sites can be included in the transposons. Such additional primer site(s) can include, e.g., those that are suitable for amplifying the barcoded nucleic acids and/or subjecting them to DNA sequencing. In particular embodiments, these primer(s) can be located so that barcode sequence(s) and index sequence(s), if present, are amplified and/or sequenced together with their associated nucleic acid segment (i.e., the segment of sample nucleic acids adjacent to the location of transposon insertion). Thus, for example, each transposon can additionally include a second primer binding site, which can be located, e.g., inside of the first transposon barcode sequence and the first index sequence, if present. This orientation is shown in FIG. 1.

In some embodiments, it will be advantageous to include a third primer binding site in each transposon. For example, in embodiments in which each transposon includes a first transposon barcode sequence located within or adjacent to a transposon end and a second transposon barcode sequence located within or adjacent to the other transposon end, second and third primer binding sites may be included to facilitate detection of both barcodes. FIG. 1 illustrates one possible configuration in which the transposon includes:

a first index sequence adjacent to the first barcode sequence;

a second index sequence is adjacent to the second barcode sequence;

a first primer binding site is located in the stuffer sequence;

a second primer binding site is located inside of the first barcode sequence and the first index sequence; and a third primer binding site is located inside of the second barcode sequence and the second index sequence.

In some embodiments, the second and third primer binding sites are the same; in other embodiments, the second and third primer binding sites are different.

Figure 8A:
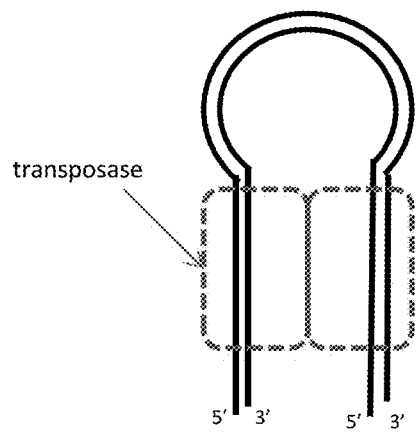
FIG. 8A-8F illustrates various possible transpososome complexes. As shown, the stuffer sequence can be double-stranded (8A), discontinuous (8B), or single-stranded (8C and 8E), optionally with a 3'-3' connection (8D) or 5'-5' connection (8F).
Figure 8B:
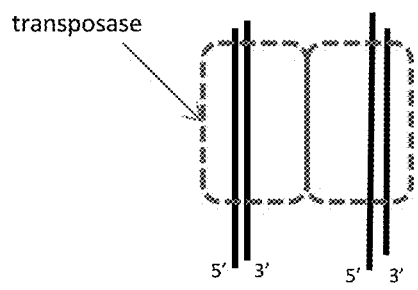
Figure 8C:
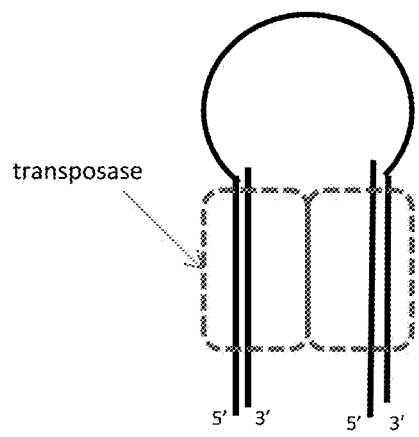
Figure 8D:
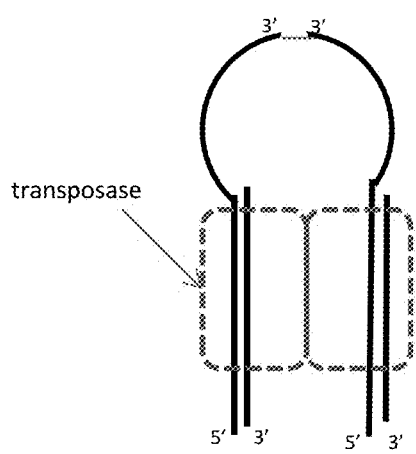
Figure 8E:
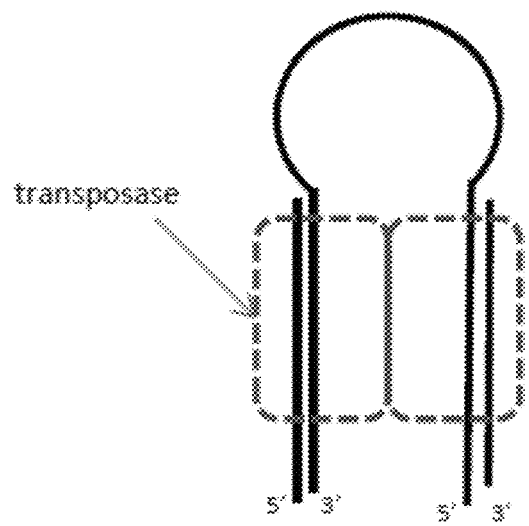
Figure 8F:
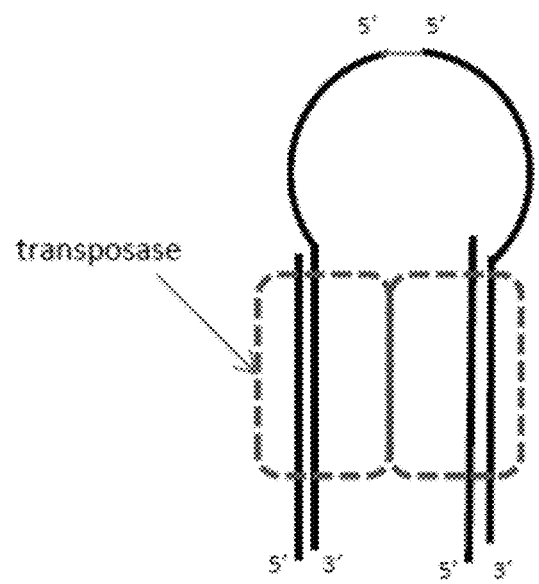

In certain embodiments, the transposon ends are double-stranded. In such embodiments, the stuffer sequence can be double-stranded (FIG. 8A), discontinuous (FIG. 8B), or single-stranded (FIGS. 8C and 8E), optionally with a 3'-3' connection (FIG. 8D) or 5'-5' connection (FIG. 8F). The stuffer sequence must be sufficiently long to form a loop when the transposon ends are complexed with a suitable transposase. Because single-stranded DNA is more flexible than double-stranded DNA, a single-stranded stuffer sequence can be considerably shorter (e.g., about 50 nucleotides) than double-stranded stuffer sequence (e.g., about 500 nucleotides). Thus, illustrative stuffer sequences can range from about 45 to about 1000 nucleotides or more, e.g., about: 45, 50, 55, 60, 65, 70, 75, 80, 85, 90, 95, 100, 125, 150, 175, 200, 225, 250, 275, 300, 325, 350, 375, 400, 425, 450, 475, 500, 600, 650, 700, 725, 750, 800, 850, 900, 950, 1000, or can fall within any range bounded by any of these values, e.g. 50-550 nucleotides.

The transposon ends must include the nucleotide sequences (the "transposon end sequences") that are necessary to form the complex with a transposase or integrase enzyme that is functional in an in vitro transposition reaction. A transposon end forms a "complex" or a "synaptic complex" or a "transposome complex" or a "transposome composition with a transposase or integrase that recognizes and binds to the transposon end, and which complex is capable of inserting or transposing the transposon end into target DNA with which it is incubated in an in vitro transposition reaction. A double-stranded transposon end exhibits two complementary sequences consisting of a "transferred transposon end sequence" or "transferred strand" and a "non-transferred transposon end sequence," or "non-transferred strand." For example, one transposon end that forms a complex with a hyperactive Tn5 transposase (e.g., EZ-Tn5™ Transposase, EPICENTRE Biotechnologies, Madison, Wis., USA) that is active in an in vitro transposition reaction comprises a transferred strand that has a "transferred transposon end sequence" as follows: 5' AGATGTGTATAAGAGACAG 3' (SEQ ID NO:19) and a non-transferred strand that has a "non-transferred transposon end sequence" as follows: 5' CTGTCT CTTATACA-CATCT 3' (SEQ ID NO:20). Different transposases utilize transposon ends that differ in length and sequence. For example, whereas the Tn5 end requires about 17 nucleotides, the mu end requires about 30 nucleotides, and the Tn7 end requires about 50 nucleotides. Although, the length appears to be important for function, the base composition will tolerate some variations (Goldhaber-Gordon, et. al. J. Biol. Chem. 2002, 277:7703-7712, which is hereby incorporated by reference for its description of variable positions), as described further below.

Figure 5:
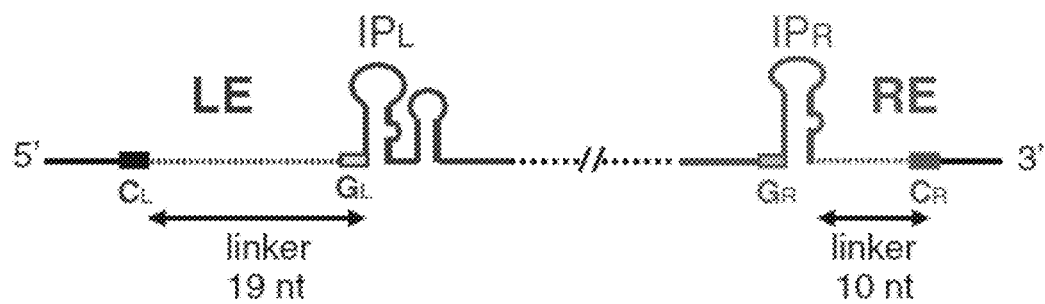
FIG. 5 shows the structure of an illustrative single-stranded transposon (IS408). LE is typically arranged from 5' to 3' with three parts: LE Linker, GL, and IPL. The LE linker resides 3' to the right cleavage site, CL. TnpA cuts between CL and the linker. IPL is the subterminal secondary structure, GL serves as the guide sequence for LE; GL interacts with CL for proper transposase activity. RE consists of three parts as well, arranged from 5' to 3' with three parts: IPR, RE Linker, and CR. GR serves as the guide sequence for RE, GR interacts with CR for proper transposase activity. CL and CR define the right and left cutting sites respectively.

In particular embodiments, the transposon ends are single strands that form hairpin structures. The structure of single-stranded transposons is different from that of double-stranded transposons, which have two double-stranded DNA regions as transponson ends (TE). In most cases, two ends of double-stranded transposons are identical in sequence but may be slightly different. In contrast, single-stranded transposons have single-stranded left (LE) and single-stranded right (RE) ends of different sequence, shown in FIG. 5. The sequences of LE and RE adopt secondary structure of their own, LE having two stem-loops, and RE having one stem-loop.

LE is typically arranged from 5' to 3' with three parts: LE Linker, GL, and IPL. There are neither primary sequence, nor secondary structure, requirements for the LE linker; the length is 19 bases for IS408. It resides 3' to the right cleavage site, CL. TnpA cuts between CL and the linker. IPL is the subterminal secondary structure, GL serves as the guide sequence for LE; GL interacts with CL for proper transposase activity.

RE consists of three parts as well, arranged from 5' to 3' with three parts: IPR, RE Linker, and CR. There are neither primary sequence, nor secondary structure, requirements for the RE linker; the length is 10 bases long for IS408. GR serves as the guide sequence for RE, GR interacts with CR for proper transposase activity. CL and CR define the right and left cutting sites respectively. The sequences are specific for each transposase. They are TTAC, and TCAA respectively for IS408, but are pentamers of different sequences for other single-stranded transposes.

If single-stranded transposon ends are employed for transposition, the ends typically flank a single-stranded stuffer sequence.

Transposases and Transposition

A "transposition reaction" or "transposition" is a reaction wherein one or more transposon ends are inserted into sample nucleic acids at random sites or almost random sites. Essential components in a transposition reaction are a transposase and DNA oligonucleotides that exhibit the nucleotide sequences of the transposon end, including the transferred transposon end sequence and its complement, the non-transferred transposon end sequence, as well as other components needed to form a functional transposition complex (i.e., a loaded transposase). Suitable transposition complexes for use in the methods described herein include, e.g., a transposition complex formed by a hyperactive Tn5 transposase and a Tn5-type transposon end (Goryshin, I. and Reznikoff, W. S., J. Biol. Chem., 273: 7367, 1998, which is hereby incorporated by reference for this description) or by a MuA transposase and a Mu transposon end comprising R1 and R2 end sequences (Mizuuchi, K., Cell, 35: 785, 1983;

Savilahti, H, et al., EMBO J., 14: 4893, 1995, which is hereby incorporated by reference for this description). However, any transposition system that is capable of inserting a transposon end in a random or in an almost random manner with sufficient efficiency to mark sample nucleic acids as described herein can be used in the present invention.

Examples of transposition systems known in the art include, but are not limited to, *Staphylococcus aureus*, Tn552 (Colegio O R et al., J. Bacteriol., 183: 2384-8, 2001; Kirby C et al., Mol. Microbial., 43: 173-86, 2002), Ty1 (Devine S E, and Boeke J D., Nucleic Acids Res., 22: 3765-72, 1994 and International Patent Application No. WO 95/23875), Transposon Tn7 (Craig, N L, Science. 271: 1512, 1996; Craig, N L, Review in: Curr Top Microbial Immunol., 204: 27-48, 1996), Tn/O and IS1O (Kleckner N, et al., Curr Top Micro biol Immunol., 204: 49-82, 1996), Mariner transposase (Lampe D J, et al., EMBO J., 15: 5470-9, 1996), Te1 (Plasterk R H, Curr Top Microbial Immunol, 204: 125-43, 1996), P Element (Gloor, G B, Methods Mol. Biol., 260: 97-114, 2004), Tn3 (Ichikawa H, and Ohtsubo E., J Biol. Chem. 265: 18829-32, 1990), bacterial insertion sequences (Ohtsubo, F and Sekine, Y, Curr. Top. Microbial. Immunol. 204: 1-26, 1996), retroviruses (Brown P 0, et al., Proc Natl Acad Sci USA, 86: 2525-9, 1989), and retrotransposon of yeast (Boeke J D and Corces V G, Annu Rev Microbial. 43: 403-34, 1989).

Recently, a group of transposases were discovered to be capable of transposition of single-stranded DNA into single-stranded target. These transposases are encoded by the tnpA gene from IS200, IS605, IS608 and ISrad, where IS stands for insertion sequences. Single-stranded transposases, TnpA, are not related to the well-known and best characterized double-stranded transposases, but are members of the large HUH (histidine-hydrophobic-histidine) endonuclease family that includes viral Rep proteins, conjugative plasmid relaxases and rolling circle replication initiator proteins. HUH nucleases use a catalytic tyrosine residue to attack the target phosphodiester bond creating a covalent 5'phosphotyrosine enzyme-substrate intermediate. Single-stranded transposition systems that may be used in the invention are described, for example, in He, S., et al., Nucleic Acids Res., 41(5):3302-13 (2013 Mar. 1; Epub 2013 Jan. 23); He, S., et al., Nucleic Acids Res., 39(19):8503-12 (2011 October; Epub 2011 Jul. 10); Ton-Hoang, B., et al., Cell, 142(3):398-408 (2010 Aug. 6); Guynet, C., et al., Mol Cell, 29(3):302-12 (2008 Feb. 15); Barabas, O., et al, Cell, 132(2):208-20 (2008 Jan. 25); Ton-Hoang, B., et al., EMBO J., 24(18):3325-38 (2005 Sep. 21; Epub 2005 Sep. 15); Ronning, D. R., et al., Mol Cell., 20(1):143-54 (2005 Oct. 7); and Ton-Hoang, B., et al., EMBO J., 17(4):1169-81 (1998 Feb. 16).

In general, a suitable in vitro transposition system for use in the methods of described herein requires a transposase enzyme of sufficient purity, sufficient concentration, and sufficient in vitro transposition activity and a transposon end with which the transposase forms a functional complex. Suitable transposase transposon end sequences that can be used in the invention include but are not limited to wildtype or artificial transposon end sequences (see below) that form a complex with a wildtype or mutant transposase. Illustrative transposases include wildtype or mutant forms of Tn5 transposase and MuA transposase (although EZ-Tn5 transposase is significantly more efficient than an equivalent protein amount of MuA transposase), but any other transposase for which compositions and conditions for efficient in vitro transposition of defined transposon ends are known or subsequently developed can be used in the present methods.

In some embodiments, the transposon end sequences are of the smallest possible size that functions well for the intended purpose, but are large enough that the same sequence is present only rarely or preferably, is not present at all, in the sample nucleic acids. Suitable in vitro transposition systems that can be used to insert a transposon end into sample nucleic acids include, but are not limited to, those that use the EZ-Tn5™ hyperactive Tn5 Transposase available from EPICENTRE Technologies, Madison, Wis., or the HyperMu™ Hyperactive MuA Transposase from EPICENTRE or another MuA Transposase, such as that available from Finnzymes Oy, Espoo, Finland.

Transposon end oligonucleotides that have the sequences of the corresponding transposon ends can be synthesized using an oligonucleotide synthesizer or purchased from a commercial source based on information available from the respective vendors or using information well known in the art. For example, the nucleotide sequences of the hyperactive transposon mosaic end for EZ-Tn5™ transposase are presented in U.S. Patent Publication No. 2010/0120098 (which is hereby incorporated by reference for its description of transposition systems) and additional information related to EZ-Tn5™ transposase is available in the published literature and online at www.EpiBio.com from EPI-CENTRE Biotechnologies, Madison, Wis., USA.

In some embodiments, the insertion of a transposon end into sample nucleic acids can also be carried out in vivo. If transposition is carried out in vivo, transposition into the sample nucleic acids is preferably achieved by electroporating a synaptic complex of a transposase and a suitable transposon end composition into the host cell as described in U.S. Pat. No. 6,159,736 (which is hereby incorporated by reference for this description). This transposition method is exemplified by employing a transposition complex formed by a hyperactive Tn5 transposase and a suitable Tn5-type transposon end composition using methods similar to those described by Goryshin, I. and Reznikoff, W. S. (J. Biol. Chem., 273: 7367, 1998) or a transposition complex formed by HyperMu™ Hyperactive MuA Transposase (EPICENTRE, Madison, Wis.) and a suitable MuA transposon end composition that exhibits the R1 and R2 end sequences recognized by the transposase. Suitable synaptic complexes or Transposome™ complexes (EPICENTRE) between a transposon end composition and a transposase can be made as described in U.S. Pat. No. 6,159,736 and related patents of Goryshin and Reznikoff, or as described in product literature for Tn5-type EZ-Tn5™ Transposome™ complexes or for HyperMu™ MuA Transposome™ complexes from EPICENTRE Technologies, Madison, Wis.

Transposition reactions can be carried out in any suitable reaction vessel, such as, for example, in wells of a microtiter plate or in compartments of a microfluidic device, such as those described below.

Figure 7:
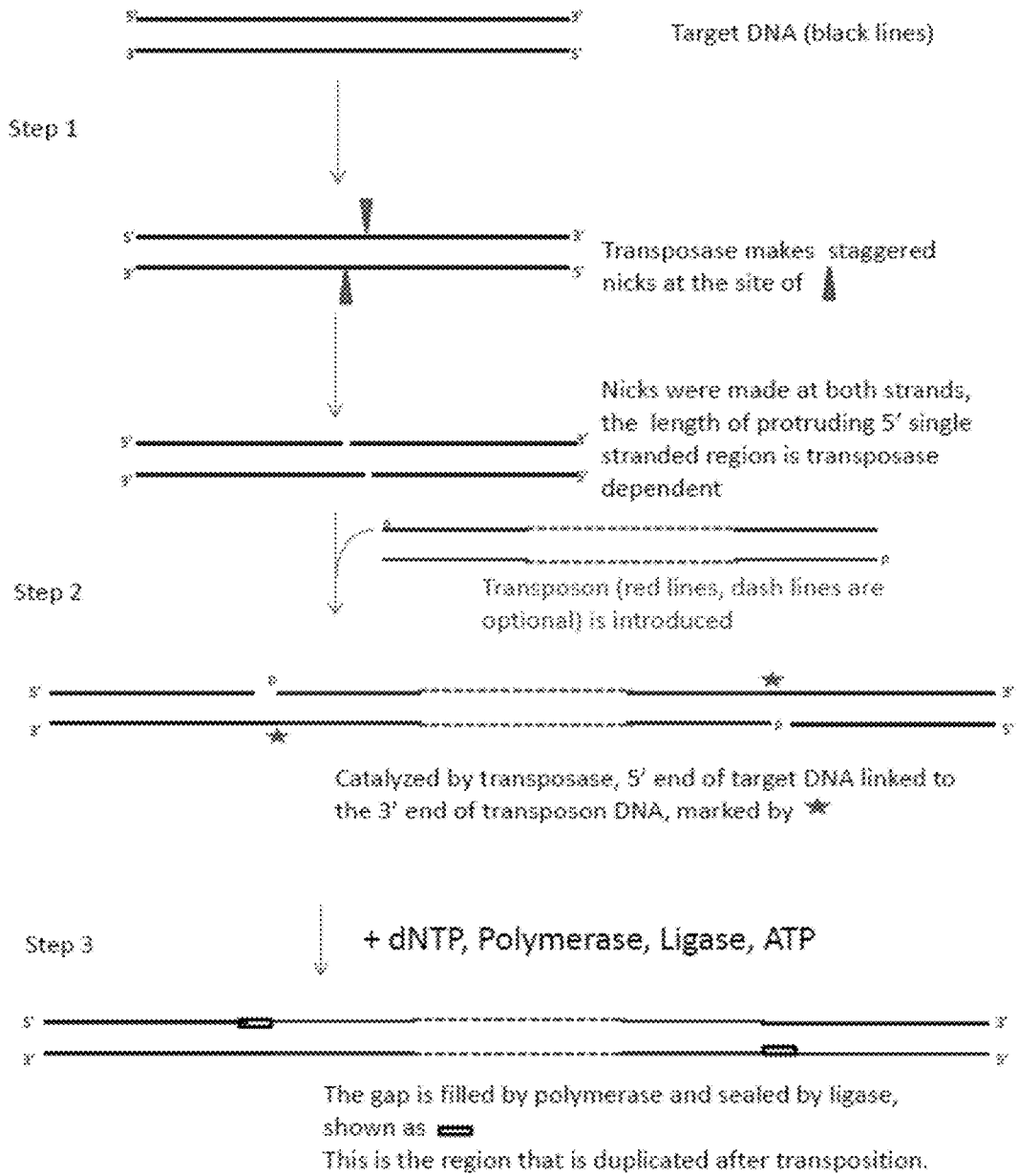
FIG. 7 shows an illustrative in vitro transposition reaction for a double-stranded transposon.

An illustrative in vitro transposition reaction in which a double-stranded transposon inserts into double-stranded target DNA is shown schematically in FIG. 7. First, a loaded transposase attacks the target DNA by making two staggered nicks on the opposite strands of the DNA. The distance between two nicks is transposase dependent. For example, it is 5 bases for MuA, while it is 7 bases for Tn5. Then, the same loaded transposase links the 3' end of transposon DNA to the 5' end of target DNA, leaving a gap of 5 bases for Mu or 7 bases for Tn5 on the other strand at each joint. In some embodiments, this gap is filled and sealed using common molecular biological techniques that are known to those skilled in art. For example, the gap can be filled by polymerase using dNTPs, and sealed by ligase as shown as Step 3 of FIG. 7. These two gaps are two identical repeated sequences, which can be used as barcodes.

Sample Nucleic Acids

Preparations of sample nucleic acids can be obtained from any source and prepared using conventional methods known in the art, with the choice of a specific method depending on the source, the nature of nucleic acid, and similar factors. The sample nucleic acids need not be in pure form, but are typically sufficiently pure to allow the reactions of interest to be performed.

In particular, nucleic acids useful in the methods described herein can be extracted and/or amplified from any source, including bacteria, protozoa, fungi, viruses, organelles, as well higher organisms such as plants or animals, particularly mammals, and more particularly humans. Nucleic acids can be extracted or amplified from cells, bodily fluids (e.g., blood, a blood fraction, urine, etc.), or tissue samples by any of a variety of standard techniques. Illustrative samples include samples of plasma, serum, spinal fluid, lymph fluid, peritoneal fluid, pleural fluid, oral fluid, and external sections of the skin; samples from the respiratory, intestinal genital, and urinary tracts; samples of tears, saliva, blood cells, stem cells, or tumors. For example, samples of fetal DNA can be obtained from an embryo or from maternal blood. Samples can be obtained from live or dead organisms or from in vitro cultures. Illustrative samples can include single cells, formalin-fixed and/or paraffin-embedded tissue samples, and needle biopsies. Nucleic acids useful in the methods described herein can also be derived from one or more nucleic acid libraries, including cDNA, cosmid, YAC, BAC, P1, PAC libraries, and the like. Nucleic acids useful in the methods described herein can also be single-stranded DNA, such as viral DNA, cDNA reverse transcribed from viral RNA, or cellular RNA.

In certain embodiments, the above-described methods are used in the context of analyzing single cells, and, in some embodiments, single-cell analysis is carried out in a population of cells.

Single-cell analysis can be carried out using any method whereby the nucleic acids of a single cell can be subjected to transposon-mediated barcoding separately from any other cell; i.e., at/in a reaction site that is sufficient separate from the reaction site for any other cell. In some embodiments, single-cell analysis entails capturing cells of a population in separate reaction volumes to produce a plurality of separate reaction volumes containing only one cell each. Cell-containing separate reaction volumes can be formed in droplets, in emulsions, in vessels, in wells of a microtiter plate, or in compartments of a matrix-type microfluidic device. In illustrative embodiments, the separate reaction volumes are present within individual compartments of a microfluidic device, such as, for example, any of those described in U.S. Patent Publication No. 2013/0323732, published May 12, 2013, Anderson et al. (hereby incorporated by reference for their descriptions of single-cell analysis methods and systems). The $C_1$™ Single-Cell Auto Prep System available from Fluidigm Corporation (South San Francisco, Calif.) provides bench-top automation of the multiplexed isolation, lysis, and reactions on nucleic acids from single cells in an "integrated fluidic circuit (IFC)" or "chip" and is therefore well-suited for performing transposon-mediated barcoding of nucleic acids from single cells. In particular, the $C_1$ Single-Cell Auto Prep Array™ IFC is a matrix-type microfluidic device that facilitates capture and highly paralleled preparation of 96 individual cells. When used properly, each capture site within the chip captures one single cell. Sometimes, a site may capture zero, two, or more cells; however, the exact number of captured cells in each captured site of a $C_1$ chip is easily verified at high confidence and easily documented in a microscopic picture. In certain embodiments, cells are captured and transposon-mediated barcoding is carried out in each separate reaction volume to produce barcoded nucleic acid molecules, which are analyzed, most conveniently by DNA sequencing, be it Sanger sequencing, next-generation sequencing, or third-generation sequencing, optionally after WGA.

In some embodiments, transposon-mediated barcoding and/or any subsequent steps, such as WGA or other amplification, is carried out in a microfluidic device having reaction chambers ranging from about 2 nL to about 500 nL. The lower the reaction chamber volume, the higher the effective concentration of any target nucleic acid and the greater the number of individual assays that may be run (either using different probe and primer sets or as replicates of the same probe and primer sets or any permutation of numbers of replicates and numbers of different assays). In one embodiment, the reaction chamber is from about 2 nL to about 50 nL, preferably 2 nL to about 25 nL, more preferably from about 4 nL to about 15 nL. In some embodiments, the reaction chamber volume is 5 nL, 6, nL, 7 nL, 8 nL, 9 nL, 10 nL, 11 nL, or 12 nL, or falls within any range bounded by any of these values.

In various embodiments, a microfluidic device having from about 5 to about 96 separate reaction sites or chambers is employed to carry out one or more of the reactions described herein, particularly from about 5 to about 48 chambers, more particularly from about 8 to about 48 chambers, and even more particularly from about 10 to about 48 chambers. In some embodiments the microfluidic device can have greater than 10, greater than 12, greater than 15, greater than 17, greater than 20, greater than 23, greater than 25, greater than 28, greater than 30, greater than 33, greater than 35, greater than 37, greater than 40, greater than 45 greater than 48, greater than 50, greater than 53, greater than 55, greater than 58, greater than 60, greater than 63, greater than 65, greater than 68, greater than 70, greater than 73, greater than 75, greater than 78, greater than 80, greater than 83 greater than 85, greater than 88, greater than 90, greater than 93, or greater than 96 sites/chambers, or greater than 1000 sites/chambers.

In some embodiments, the analysis of the barcoded nucleic acids can be carried out in the same reaction volumes in which transposon-mediated barcoding is carried out. In particular embodiments, however, it is advantageous to recover the contents of the separate reaction volumes after barcoding for subsequent analysis. For example, if a nucleic acid amplification is carried out in the separate reaction volumes, it may be desirable to recover the contents for subsequent analysis, e.g., by DNA sequencing. The contents of the separate reaction volumes may be analyzed separately and the results associated with the cells present in the original reaction volumes. In embodiments, in which separate reaction volumes may contain more than one cell, single-cell analysis can be achieved by identifying reaction volume(s) containing only a single cell and only analyzing the contents of those reaction volumes.

In particular embodiments, the cell/reaction volume identity can be encoded in the reaction product using one or more (e.g., a combination of) transposon indexes, for example, as discussed above. Cell/reaction indexes can then be determined together with their linked barcoded nucleic acid molecules to associate these molecules with the cell/reaction volume from which they were derived. In certain embodiments, sets of separate reaction volumes are encoded, such that each reaction volume within the set is uniquely identifiable, and then pooled, with each pool then being analyzed separately from any other pool. Where single cell analysis is desired, but reaction volumes may contain more than a single cell, such embodiments may also entail determining which reaction volume(s) contained only a single cell. Because the corresponding cell/reaction index for each reaction volume is known, the results from the single-cell reaction volumes can be discriminated from the multi-cell reaction volumes.

The methods described herein can be used to analyze nucleic acids from any type of cells, e.g., any self-replicating, membrane-bounded biological entity or any non-replicating, membrane-bounded descendant thereof. Non-replicating descendants may be senescent cells, terminally differentiated cells, cell chimeras, serum-starved cells, infected cells, non-replicating mutants, anucleate cells, etc. Cells used in the methods described herein may have any origin, genetic background, state of health, state of fixation, membrane permeability, pretreatment, and/or population purity, among other characteristics. Suitable cells may be eukaryotic, prokaryotic, archaeon, etc., and may be from animals, plants, fungi, protists, bacteria, and/or the like. In illustrative embodiments, human cells are analyzed. Cells may be from any stage of organismal development, e.g., in the case of mammalian cells (e.g., human cells), embryonic, fetal, or adult cells may be analyzed. In certain embodiments, the cells are stem cells. Cells may be wildtype; natural, chemical, or viral mutants; engineered mutants (such as transgenics); and/or the like. In addition, cells may be growing, quiescent, senescent, transformed, and/or immortalized, among other states. Furthermore, cells may be a monoculture, generally derived as a clonal population from a single cell or a small set of very similar cells; may be presorted by any suitable mechanism, such as affinity binding, FACS, drug selection, etc.; and/or may be a mixed or heterogeneous population of distinct cell types. Cells may be disrupted, partially (e.g., permeabilized) to allow uptake of transposons or fully (e.g., lysed) to release interior components.

One advantage of the methods described herein is that they can be used to analyze virtually any number of single cells. In various embodiments, the number of single cells analyzed can be about 10, about 50, about 100, about 500, about 1000, about 2000, about 3000, about 4000, about 5000, about 6000, about 7,000, about 8000, about 9,000, about 10,000, about 15,000, about 20,000, about 25,000, about 30,000, about 35,000, about 40,000, about 45,000, about 50,000, about 75,000, or about 100,000 or more. In specific embodiments, the number of cells analyzed can fall within a range bounded by any two values listed above.

Whole Genome Amplification

In some embodiments, barcoded nucleic acid molecules are subjected to a whole genome amplification (WGA) procedure to generate more DNA for subsequence analysis. Any available WGA procedure can be employed to amplify barcoded nucleic acid molecules. Suitable WGA procedures include, but are not limited to:

Primer extension PCR (PEP) and improved PEP (I-PEP)—PEP typically uses Taq polymerase and 15-base random primers that anneal at a low stringency temperature. The use of Taq polymerase implies that the maximal product length is about 3 kb.

Degenerated oligonucleotide primed PCR (DOP-PCR)—DOP-PCR is well-established, widely accepted, and technically straightforward method. DOP-PCR uses Taq polymerase and semi-degenerate oligonucleotides that bind at a low annealing temperature at approximately one million sites in the human genome. The first cycles are followed by a large number of cycles with a higher annealing temperature, allowing only for the amplification of the fragments that were tagged in the first step. DOP-PCR generates, like PEP, fragments that are in average 400-500 bp, with a maximum size of 3 kb, although a DOP-PCR method that was able to produce fragments up to 10 kb had been described.

Ligation-mediated PCR (LMP)—LMP uses endonuclease or chemical cleavage to fragment the genomic DNA sample and linkers and primers for its amplification. It was first described by Ludecke and coworkers and was later adapted for the WGA of small quantities of gDNA and single cells. Rubicon Genomics commercializes different kits (Omniplex) that allow for the amplification of RNA, DNA and methylated DNA sequences. Advantages include that the method is able to amplify degraded DNA and that all steps are performed in the same tube. A limitation is that it generates fragments only up to 2 kb.

T7-based linear amplification of DNA (TLAD)—TLAD is a variant on the protocol originally designed to amplify mRNA, which has been adapted for WGA. It uses Alu I restriction endonuclease digestion and a terminal transferase to add a polyT tail on the 3' terminus. A primer is then used with a 5' T7 promoter and a 3' polyA tract, and Taq polymerase is used to synthesize the second strand. Then the sample is submitted to in vitro transcription reaction and posterior reverse transcription. A major advantage is that TLAD does not introduce sequence and length-dependent biases.

Multiple displacement amplification (MDA)—MDA is a non-PCR-based isothermal method based on the annealing of random hexamers to denatured DNA, followed by strand-displacement synthesis at constant temperature. It has been applied to small genomic DNA samples, leading to the synthesis of high molecular weight DNA with limited sequence representation bias. As DNA is synthesized by strand displacement, a gradually increasing number of priming events occur, forming a network of hyper-branched DNA structures. The reaction can be catalyzed by the Phi29 DNA polymerase or by the large fragment of the Bst DNA polymerase. The Phi29 DNA polymerase possesses a strand displacement activity and a proofreading activity resulting in error rates 100 times lower than the Taq polymerase.

The Rapisome™ pWGA (protein-primed WGA) is a whole genome amplification process marketed by BioHelix (BioHelix Corporation, A Quidel Company. 500 Cummings, Suite 5550. Beverly, Mass. 01915). Instead of using primers, the kit uses primase to synthesize primers on-site, generating multiple initiation sites for random, whole genome amplification.

Kits for WGA are available commercially from, e.g., Qiagen, Inc. (Valencia, Calif. USA), Sigma-Aldrich (Rubicon Genomics; e.g., Sigma GenomePlex® Single Cell Whole Genome Amplification Kit, PN WGA4-50RXN). The WGA step of the methods described herein can be carried out using any of the available kits according to the manufacturer's instructions.

In particular embodiments, the WGA step is limited WGA, i.e., WGA is stopped before a reaction plateau is reached. Typically, WGA is performed for more than two amplification cycles. In certain embodiments, WGA is performed for fewer than about 10 amplification cycles, e.g., between four and eight cycles, inclusive. However, WGA can be performed for 3, 4, 5, 6, 7, 8, or 9 cycles or for a number of cycles falling within a range defined by any of these values.

In embodiments in which a WGA primer binding site is included in the transposon, e.g., in the stuffer sequence or within a transposon end, WGA can be carried out using a primer that binds to this site. For many applications, it will be most convention to use transposons that all include the same primer binding site to facilitate WGA using just one primer. However, different transposons may carry different primer binding sites, if desired, in which case multiple corresponding primers can be employed in WGA. If multiple primers are employed, WGA can be carried out with all primers present in the reaction mixture or multiple separate reactions can be performed using different primers. When WGA is primed from a site in the transposon, the average transposon density should be sufficient that the particular WGA procedure used will proceed efficiently. In various embodiments, the values and ranges given above for barcode density define suitable transposon densities for WGA priming from a site in the transposon stuffer sequence.

In embodiments in which a primase recognition sequence is included in the transposon stuffer sequence, pWGA can be carried out using a primase that binds to these sites introduced to genome by transposition.

WGA can be carried out in the same reaction mixture as transposon barcoding or barcoded nucleic acid molecules can be recovered and then added to new WGA reaction mixture. When WGA is carried out in the same reaction mixture, in some embodiments, the transposase is inactivated, e.g., using EDTA and/or heat denaturation. In either case, WGA can be carried out using a microfluidic device, such as any of those described above.

Analysis of Barcoded Nucleic Acid Molecules

In some embodiments, the barcoded nucleic acid molecules are analyzed, optionally after WGA, to determine the pattern of barcodes associated with a given nucleic acid segment. Any available method capable of making this determination can be employed; however, next-gen DNA sequencing is currently the most convenient for this analysis.

In certain embodiments, barcoded nucleic acid molecules are sequenced, optionally after WGA, to determine which transposon barcodes are associated with which nucleic acid segments. Although any available DNA sequencing technique can be employed, high-throughput ("next-generation" or "third generation") sequencing techniques are preferred for many applications.

Next-generation sequencing techniques parallelize the sequencing process, producing thousands or millions of sequences concurrently. Illustrative next-generation techniques include, but are not limited to, Massively parallel signature sequencing (MPSS), Polony sequencing, 454 pyrosequencing, Illumina (Solexa) sequencing, SOLiD sequencing, Ion Torrent semiconductor sequencing, DNA nanoball sequencing, and Heliscope single molecule sequencing.

Many next-generation sequencing techniques include an amplification step prior to DNA sequencing. For example, emulsion amplification or bridge amplification can be carried out. Emulsion PCR (emPCR) isolates individual DNA molecules along with primer-coated beads in aqueous droplets within an oil phase. PCR produces copies of the DNA molecule, which bind to primers on the bead, followed by immobilization for later sequencing. emPCR is used in the methods by Marguilis et al. (commercialized by 454 Life Sciences, Branford, Conn.), Shendure and Porreca et al. (referred to herein as "454 sequencing;" also known as "polony sequencing") and SOLiD sequencing, (Life Technologies, Foster City, Calif.). See M. Margulies, et al. (2005) "Genome sequencing in microfabricated high-density picolitre reactors" Nature 437: 376-380; J. Shendure, et al. (2005) "Accurate Multiplex Polony Sequencing of an Evolved Bacterial Genome" Science 309 (5741): 1728-1732. In vitro clonal amplification can also be carried out by "bridge PCR," where fragments are amplified upon primers attached to a solid surface. Braslaysky et al. developed a single-molecule method (commercialized by Helicos Biosciences Corp., Cambridge, Mass.) that omits this amplification step, directly fixing DNA molecules to a surface. I. Braslaysky, et al. (2003) "Sequence information can be obtained from single DNA molecules" Proceedings of the National Academy of Sciences of the United States of America 100: 3960-3964.

DNA molecules that are physically bound to a surface can be sequenced in parallel. "Sequencing by synthesis," like dye-termination electrophoretic sequencing, uses a DNA polymerase to determine the base sequence. "Pyrosequencing" uses DNA polymerization, adding one nucleotide at a time and detecting and quantifying the number of nucleotides added to a given location through the light emitted by the release of attached pyrophosphates (commercialized by 454 Life Sciences, Branford, Conn.). See M. Ronaghi, et al. (1996). "Real-time DNA sequencing using detection of pyrophosphate release" Analytical Biochemistry 242: 84-89. Reversible terminator methods (commercialized by Illumina, Inc., San Diego, Calif. and Helicos Biosciences Corp., Cambridge, Mass.) use reversible versions of dye-terminators, adding one nucleotide at a time, and detecting fluorescence at each position in real time, by repeated removal of the blocking group to allow polymerization of another nucleotide.

In one embodiment of the detection-by-primer extension method, which can conveniently be carried out on the 454 sequencing platform, the first and second primer extension reactions are carried out sequentially in at least two cycles of primer extension. In particular, a first cycle of primer extension is carried out using the first primer that anneals to the first nucleotide tag, and a second cycle of primer extension is carried out using the second primer that anneals to the second nucleotide tag. All deoxynucleoside triphosphates (dNTPs) are provided in each cycle of primer extension. The incorporation of any dNTP into a DNA molecule produces a detectable signal. The signal detected in the first cycle indicates the presence of the first target nucleic acid in the nucleic acid sample, whereas the signal detected in the second cycle indicates the presence of the second target nucleic acid in the nucleic acid sample. Thus, each target nucleic acid (e.g., mutation) can be detected with only a single cycle of the sequencing platform.

So-called "third-generation" sequencing techniques aim to increase throughput and decrease the time to result and cost by reading sequence directly from single DNA molecules, thus eliminating the need for template amplification as in the case of bridge PCR or emulsion PCR. Illustrative third-generation techniques include Nanopore DNA sequencing, Tunneling currents DNA sequencing, Sequencing by hybridization, Sequencing with mass spectrometry, Microfluidic Sanger sequencing, Microscopy-based techniques, RNA polymerase (RNAP) sequencing, In vitro virus high-throughput sequencing.

A substantial amount of the labor associated with high-throughput sequencing techniques is in the preparation of a DNA sequencing library. Library construction can be simplified using a transposase-based in vitro shotgun method termed "tagmentation," in which the DNA to be sequenced is simultaneously fragmented and tagged with transposon ends to introduce sequences that facilitate subsequent sequencing.

In some embodiments, "tagmentation" library construction methods can be used to barcode nucleic acids, such as DNA of single cells, according to the methods described above.

Kit Containing Sets of Transposons for Marking Target DNA Sequences

Kits according to the invention can include one or more reagents useful for practicing one or more assay methods described herein. A kit generally includes a package with one or more containers holding the reagent(s), as one or more separate compositions or, optionally, as admixture where the compatibility of the reagents will allow. The kit can also include other material(s) that may be desirable from a user standpoint, such as a buffer(s), a diluent(s), a standard(s), and/or any other material useful in sample processing, washing, or conducting any other step of the assay. In specific embodiments, the kit includes one or more matrix-type microfluidic devices discussed above.

In particular embodiments, a kit according to the invention can include a set of two or more functional transposons (i.e., that are each capable of being inserted into nucleic acids by a transposase), wherein each transposon includes a different first transposon barcode sequence and transposon ends flanking a stuffer sequence having a primer binding site. In certain embodiments, the transposons each include the same first primer binding site in the stuffer sequence. In various embodiments, the number of transposons in the set is: 2, 3, 4, 5, 6, 7, 8, 9, 10, 15, 20, 25, 30, 35, 40, 45, or 50 or more, each of which includes a unique barcode sequence. In some embodiments, the number of transposons in a kit falls within a range bounded by any of these values, e.g., 5-25 or 10-15.

In certain embodiments, the kit includes at least two sets of two or more transposons, wherein each transposon within a set includes a barcode sequence that is different from all other barcodes in the set, but wherein each set of transposons includes the same set of barcode sequences as the other set(s) of transposons. Each transposon within a set can have an index sequence that is the same for all transposons within a set, but different than in the other set(s) of transposons. In various embodiments, each set can include any number of transposons, as described above, and the kit can include any number of sets, e.g., 2, 3, 4, 5, 6, 7, 8, 9, 10, 15, 20, 25, 30, 35, 40, 45, 50, 60, 70, 80, 90, 100 or more. In some embodiments, the number of transposon sets in a kit falls within a range bounded by any of these values, e.g., 10-100 or 40-50. In some embodiments, each set of transposons is provided a mixture in a single container.

Such kits can also, optionally, include one or more transposases capable of incorporating the transposons into sample nucleic acids. In some embodiments, the transposase(s) are packaged with their corresponding transposons. In particular embodiments, the transpose(s) are loaded with their corresponding transposons.

Transposon Ends Containing Barcodes

In certain embodiments, the invention also provides artificial transposon ends that are useful in the above and other methods for introducing barcodes/indexes into sample nucleic acids. "Transposon ends have been found to have positions within the transposon end that can tolerate some degree of variation. Transposon barcodes can be introduced into such positions by substituting each of at least two nucleotides of the corresponding wildtype transposon end sequence with a different nucleotide to produce a transposon barcode.

Figure 6:
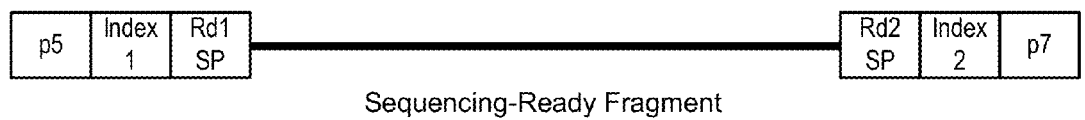
FIG. 6 shows the structure of a fragment ready for sequencing on the Illumina DNA sequencing platform. Sequencing primers anneal to the sites labeled p5 or p7 and prime sequencing through barcodes (Index1 or Index2) and transposon ends (Rd1 SP or Rd2 SP) before they start to read target sequence.

One application for transposon ends including barcodes is in DNA sequencing libraries prepared using transposons, such as tagmentation, in which the DNA to be sequenced is simultaneously fragmented and tagged with transposon ends to introduce sequences that facilitate subsequent sequencing. The way in which this technique is conventionally performed for the Illumina sequencing platform produces tagged fragments having the structure shown in FIG. 6. In this structure, sequencing primers (e.g. p5 or p7 in this case) prime sequencing through barcodes (e.g. Index1 or Index2 in this case) and transposon ends (e.g. Rd1 SP or Rd2 SP in this case) before they start to read target sequence. Accordingly, very high quality reads are wasted on known sequence, instead of being used for unknown sequence. By putting the barcodes into the non-essential positions of the transposon ends, one can minimize wasted sequencing capacity.

Specifically, in the case of mu transposon, for example the possible non-essential positions available for substitution are listed below (using the same numbering as Goldhaber-Gordon, et. al. J. Biol. Chem. 2002, 277:7703-7712):

| Position: | | | | | | | | | | | | | |
|---|---|---|---|---|---|---|---|---|---|---|---|---|---|
| 3 | 4 | 5 | 6 | 9 | 13 | 15 | 16 | 17 | 19 | 20 | 21 | 26 | 28 |
| Base: N | N | N | Y | N | Y | N | R | N | R | Y | R | N | N | where N = any base; Y = pyrimidine; R = purine

Accordingly, the mu transposon end can accommodate barcodes having 2, 3 or 4 contiguous bases or, if non-contiguous positions are employed for barcoding, barcodes can have 5, 6, 7, 8, 9, 10, 11, 12, 13, or 14 bases, yielding a very large number of different possible barcodes. Variable positions for other transposon ends are either known or can be determined empirically, and the number of variable positions may be larger or smaller than for the mu transposon.

Notably, some positions can tolerate any base substitution, and other positions require that the substituted base be a pyrimidine or a purine. The number of positions that are required for barcodes will depend upon the application (see above for a discussion of considerations related to barcodes). For example, if position 3, 4, and 5 are used for barcodes, the 3' end of sequencing primer may end at position 6. Such a primer would prime the sequencing of bases for barcodes and two known bases (Position 1 and Position 2) before reaching the unknown sequences. 17 known bases have to be read before reaching the unknown sequences. Furthermore, in the above-described configuration, one primer can read both barcodes and sample nucleic acid sequence. In many applications, a very short read of the latter, e.g., 20-30 bases, is sufficient to uniquely identify the insertion site. By contrast, in the conventional Illumina template structure, two primers are required to detect the barcode-sample nucleic acid segment combination, one to read the sample nucleic acid segment and one to read the barcode. The two reads must then be linked with coordinates, which runs the risk that two reads may be linked erroneously, confounding the analysis.

Generally, a number of different transposons with different barcodes will be employed for most applications. Accordingly, in some embodiments, the invention provides a kit including a set of two or more different first artificial transposon ends, wherein different first artificial transposon ends include different barcodes. In various embodiments, the number of artificial transposon ends in the set is: 2, 3, 4, 5, 6, 7, 8, 9, 10, 15, 20, 25, 30, 35, 40, 45, or 50 or more, each of which includes a unique barcode sequence. In particular embodiments, the number of artificial transposon ends in a kit falls within a range bounded by any of these values, e.g., 5-25 or 10-15.

In some embodiments, wherein the kit additionally includes a second transposon end, wherein the same transposase for the first artificial transposon ends can incorporate the second transposon end into the sample nucleic acids, thereby forming a tagged nucleic acid molecule wherein the first and second transposon ends flank and are separated by the sample nucleic acid sequence. The second transposon end can have any nucleotide sequence so long as it retains the ability to be incorporated by the transposase. In particular embodiments, the sequence of the second transposon end is different from that of any of the first artificial transposon ends. The second transposon end can be an artificial transposon end, as discussed above, which can have the same barcode as a paired first transposon end or can have a different barcode In some embodiments, the different artificial transposon ends are packaged together, whereas in other embodiments, they are packaged separately from one another.

Such kits can also, optionally, include one or more transposases capable of incorporating the transposon ends into sample nucleic acids. In some embodiments, the transposase(s) are packaged with their corresponding transposon ends. In particular embodiments, the transpose(s) are loaded with their corresponding transposon ends.

In certain embodiments, the kit additionally includes a primer that binds within the artificial transposon ends and primes polymerization of a nucleotide sequence including the barcode, wherein a plurality of the different artificial transposon ends includes the same primer binding site. Such embodiments are useful, for example, in DNA sequence. For sequencing, the primer binding site is preferably located so as to minimize the number of bases between the primer binding site and the template to be sequenced, provided that the primer primes polymerization of a nucleotide sequence including the barcode. In illustrative embodiments, the primer binding site is adjacent, preferably, immediately adjacent (i.e., with no intervening bases), to the end of the barcode, which is adjacent, preferably immediately adjacent, to any invariant transposon end nucleotide(s), which is/are adjacent, preferably immediately adjacent, to the template to be sequenced.

Method of Using Transposon End(s) Containing Barcode(s)

Transposon ends containing barcodes can be used to introduce the barcodes into sample nucleic acids as described herein or as known in the art. In some embodiments, these transposon ends are used to generate a barcoded DNA library using methods such as those described in U.S. Patent Publication No. 2010/0120098, published May 13, 2010, by Grunenwald et al.; European Patent No. 2376517, issued Jan. 16, 2013, to Jendrisak et al.; and U.S. Patent Publication No. 2013/0023423, published Jan. 24, 2013, by Kavanagh et al.

Generally, in some embodiments, barcode-tagged nucleic acid molecules are produced by contacting sample nucleic acids with a suitable transposase loaded with a first artificial transposon end including a sequence wherein at least 2 nucleotides of the corresponding wildtype transposon end sequence have each been substituted with a different nucleotide, said substitutions defining a barcode; thereby forming a tagged nucleic acid molecule including the first artificial transposon end flanking a sample nucleic acid segment.

In certain embodiments, the transposase is loaded with a second transposon end. The second transposon end is one that the transposase is capable of incorporating into the sample nucleic acids, together with the first transpson end. The result is a tagged nucleic acid molecule wherein the first and second transposon ends flank and are separated by the sample nucleic acid segment. In particular embodiments, In particular embodiments, the sequence of the second transposon end is different from that of any of the first artificial transposon ends. The second transposon end can be an artificial transposon end, as discussed above, which can have the same barcode as a paired first transposon end or can have a different barcode.

In particular embodiments, the method includes contacting sample nucleic acids with a transposase loaded with a set of first artificial transposon ends, wherein different first artificial transposon ends have different barcodes. The transposase can be loaded with a second transposon end that has any nucleotide sequence so long as it retains the ability to be incorporated by the transposase. In some embodiments, a set of second artificial transposon ends is employed, wherein different second artificial transposon ends have barcodes that differ from the other barcodes in the set. Loaded transposases can be produced such that each transposase includes first and second artificial transposon ends bearing the same barcode. Alternatively, each transposase can include first and second transposon ends bearing different barcodes.

In some embodiments, the method additionally entails sequencing the tagged nucleic acid molecule using a primer that binds within an artificial transposon end and primes polymerization of a nucleotide sequence including the barcode.

EXAMPLES

Example 1: Types of Haploidome Determinations Using Digitized Transposons

This Example describes methods to (1) accurately count absolute copy numbers of chromosomes from single cells, (2) improve accuracy in calling SNP or SNV, and (3) hyploid typing. Specifically, a set of transposons that contain a region of nucleotide sequence that serves as barcodes for the transposons is employed to "mark" DNA. For example, a group of transposons can share one common barcode, a second group of transposons can share a different, common barcode, and a third group of transposons can share a third, common barcode. Alternatively, each transposon can have its unique barcode or unique barcode combination. Although this Example is written in terms of transposons comprising barcodes, the same results can be achieved by using non-barcoded transposons that insert at unique sites that can be distinguished by sequencing.

The molecular structure of an illustrative transposon is shown in FIG. 1. At the two ends, there are transposon ends (also called "arms") to which transposase binds, followed by insertion of the transposon into DNA. Inside the two ends are two regions for transposon barcodes (termed "transposon indexes" in FIG. 1). Optionally, inside the regions for transposon indexes are regions for "cell indexes," which are nucleotide sequences that identify the cell that was the source of the nucleic acids under analysis. Optionally, inside the regions for cell indexes are one or more primer sequences for DNA sequencing. Between sequencing primers are staffer sequence for other uses (e.g., whole genome amplification (WGA), protein-primed WGA (pWGA), etc.

I. Copy Number Determination

Figure 2A:
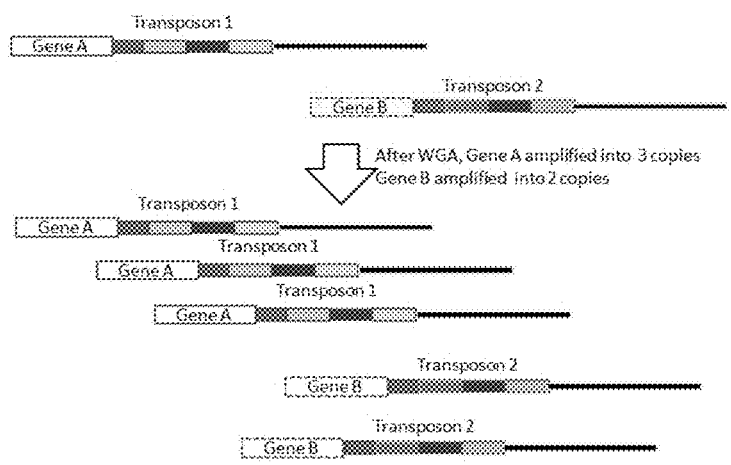
FIG. 2A-2B illustrates the use of transposon-mediated barcoding in copy number determinations. (2A) Gene A and Gene B each generate only one transposon barcode-nucleic acid segment combination, indicating that each is present in one copy; although these genes are amplified to different degrees, transposon-mediated barcoding can be used to conclude that they actually have equal copy numbers. (2B) Gene C generates three different transposon barcode-nucleic acid segment combinations, indicating that it is present in three copies.

Transposons can be used after cells are lysed, and chromosomal DNA is exposed. The amount of transposons relative to chromosomal DNA can be adjusted so that the desired density of transposon insertion can be obtained, which will vary depending on the desired resolution of the analysis. The transposon-marked genome, then, can be amplified by WGA. Typically, some regions will be over-amplified, while other regions will be under-amplified, and the over- or under-amplifications will be registered in the transposon that resides in the region. As each transposon can be individually bar-coded, the genomic sequence that associates with that transposon is bar-coded as well. The genomic sequence can be normalized to take into account differences in amplification as shown in FIG. 2A. More specifically, the number of different transposon barcode-gene patterns gives the copy number of the gene. Gene A has only one transposon barcode-gene pattern, and Gene B has only one transposon barcode-gene pattern, so each gene is present in one copy. Despite the fact that the amplification product contains 1.5 times as much Gene A as Gene B, the transposon patterns indicate that the copy number of each gene in the sample nucleic acids (pre-amplification), i.e., in the genome, was equal.

Figure 2B:
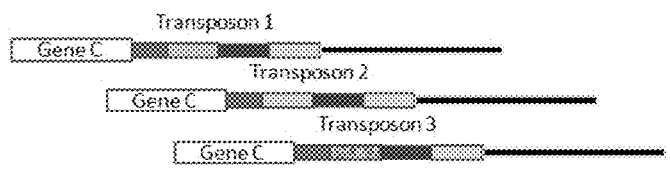

A true CNV would be detected as shown, for example, in FIG. 2B. As Gene C associates with three distinct barcoded transposons, it can be deduced that gene C is present in three copies in the genome.

Thus, one can digitally mark genomic DNA at molecular level, and by counting unique combinations of transposon barcodes in particular regions of genomic sequence, one can accurately count the copy number of loci throughout the genome. More importantly, copy number variation can be accurately determined to a very fine resolution, down to 10 Kb, 5 Kb, 2 Kb, or even to 500 bp or less. It has been reported that human genome has more copy number variation (CNV) than single nucleotide variation (SNV). Cancer cells have elevated CNV and SNV. The ability to identify CNV to a very fine resolution, therefore, has implications for understanding and diagnosing cancer and other diseases.

II. Accurate Determination of Heterzygosity and Homozygosity

In sequencing a bulk genome, or WGA-amplified genome, it is difficult ascertain that a SNP site is truly a homozygote or a heterozygote as illustrated in FIG. 3A, as allele drop out (ADO) may lead to erroneous homozygote calling. Using the method described herein, a single transposon barcode-SNP pattern obtained from a sequencing run of a diploid cell indicates ADO because two distinct transposon barcode-SNP patterns should otherwise have been observed.

More specifically, in the absence of ADO, a true homozygote should produce two different sets of transposon barcodes associated with the same SNP sequence (i.e., the "A" in FIG. 3A) because, in one "A" allele, a particular set of transposons would incorporate randomly, and in the other "A" allele, it is likely that random incorporation would produce a different set of transposons.

Alternatively, in the absence of ADO, a heterozygote should produce two different sets of transposon barcodes, each associated with a different SNP sequence, because each different allele should have two different sets of randomly incorporated transposons. This situation is shown in FIG. 3B. In the absence of the method described herein, one might conclude that the "G" allele represented a sequencing error in DNA that was homozygous "A" because the coverage of the G allele is so much lower than of the A allele.

III.a. Distinguishing Sequencing Errors from True Mutations

Figure 3C:
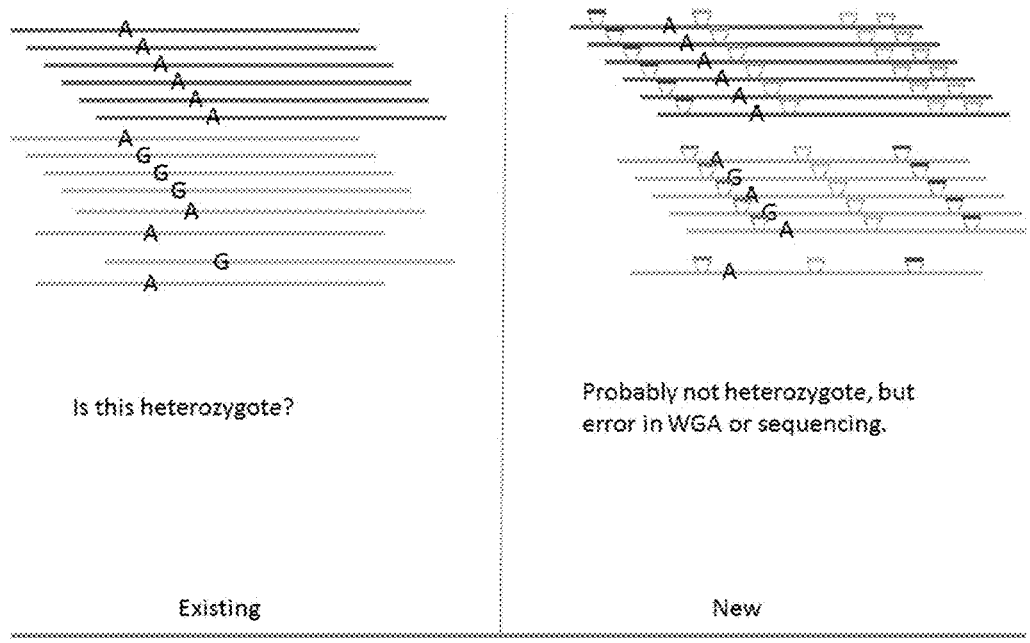

A sequencing error can be distinguished from a true mutation because a sequencing error would give rise to different SNP sequences associated with the same set of transposon barcodes. This is because each set of transposon barcodes marks a single allele, and the fact that one allele cannot have two different sequences at the same site indicates that a sequencing error has occurred. FIG. 3C illustrates a situation in which a sequencing error has occurred in one allele of a heterozygote. As expected for a heterozygote, two different transposon barcode patterns are observed. However, one pattern is associated with two different SNP sequences, namely "A" or "G," indicating that one of these nucleotides represents a sequencing error.

III.b. Improving Accuracy in Mutation Calls in Cancer Cells

A cancer cell may have 1, 2, 3, 4, 5, 6 or even more copies of one chromosome, a phenomenon called aneuploidy. If, for example, one out of 6 chromosomes has a mutation, and the sequencing coverage is 20×, the number of reads containing this mutation may be 1, 2, or 3 due to unbalanced WGA or unbalanced sequencing library construction. Accordingly, the confidence to call this mutation in conventional sequencing is not very high. In contrast, if transposon-mediated barcoding is carried out, the mutation will associate with one particular barcode, or barcode pattern (e.g., insertion site), or barcode combination, while other wildtype reads associate with five other barcodes, or barcode patterns, or barcode combinations. In this case, the mutation can be called with much greater confidence.

III.c. Improving Accuracy in Differentiating a Gene and Psuedogenes

Nanog is a retro-oncongene expressed in cancer cells. It has another nonprocessed pseudogene and ten other processed pseudogenes. Some of the pseudogenes are expressed in cancer cells. As the known pseudogenes are highly similar in primary sequence over long stretches, and there is a high probability that unidentified pseudogenes exist, discriminating one from another, especially when there is a mutation, is very challenging. As for any particular genomic region, there should be only one barcode/barcode pattern/barcode combination for one copy of that region, transposon-mediated barcoding will facilitate distinguishing one (pseudo) gene from another, thereby permitting the accurate determination of the location of any mutation (which can be identified as described in III.b. above).

IV. Digital Haploid Typing

The method described herein can also be used to associate SNPs from the same molecule of genomic DNA. When two SNPs are spaced far apart and separated by sequences that are identical in the chromosomes on which they are located (i.e., uninformative sequences), existing shot-gun sequencing methods cannot determine the phase (linkage) of the SNPs. Other labor-intensive methods have been needed to resolve this issue. As illustrated in FIG. 4, the method described herein inserts unique marks (transposon barcodes) into the uninformative region to connect the far-apart SNPs. Linked SNPs define a haplotype. Haplotype analysis is important, for example, as it has been reported that tissue donors and recipients matched for HLA haplotypes have a superior clinical outcome compared with those that are matched for alleles at individual HLA loci but not haplotype matched.

V.a. Identifying Open and Closed Alleles

When cells are lysed gently, the chromatin structure is not disturbed, and only open regions are accessible to transposition. This transposase-based technique for interrogating open chromatin is called ATAC-Seq, first reported by Buenrostro J D et al (Nat Methods. 2013 December; 10(12):1213-8. doi: 10.1038/nmeth.2688. Epub 2013 Oct. 6, Transposition of native chromatin for fast and sensitive epigenomic profiling of open chromatin, DNA-binding proteins and nucleosome position), which is hereby incorporated by reference for its description of this method.

This technique can be combined with the transposon-mediated barcoding described herein to identify both open alleles and closed alleles. First, cells are lysed gently, to maintain the chromatin in the same state as inside the cell. Then, transposons with one set of barcodes are employed to mark the open chromatin. Next, the chromatin is completely striped of histones to expose once closed chromatin. Then, transposons with a second set of barcodes are employed to mark the alleles in the formerly closed chromatin region. Barcodes can then be used to differentiate between alleles in open and closed chromatin. This is particularly useful to determine whether alleles for a particular locus are both open, or both closed, or one open and one closed.

V.b Linking Open Chromatin with Genotypes

Tumor suppressor genes are important for suppressing oncogenesis. Mutations in tumor suppressor genes may contribute to the development of cancer. For heterozygotes, having one mutant and one wildtype allele, the expression of the wild-type allele can be protective. Therefore, it may be important to determine whether the wildtype allele in an open or closed state to predict cancer risk.

A combination of methods V.a. and IV. can be employed to determine whether the wild-type allele is in open or closed state and whether the wild-type allele is associated with an open or closed enhancer, or an open or closed repressor, both of which could reside several kilobases away from the allele. More specifically, V.a. can be used to determine open/closed state in each region, and IV. can be used to determine linkage between the wildtype allele and an enhancer or repressor.

V.c. Linking Chromatin States on the Same Chromosome

A combination of V.a. and IV. is useful to determine the link between two chromosomal regions, as well as determining their states. For example, a structural gene could be open or closed at the same time that its regulatory gene could be open or closed under a particular condition. This lead to four different combinations: open structural gene-open regulator (open-open), open structural gene-closed regulator (open-closed), closed structural gene-closed regulator (closed-closed), closed structural gene-open regulator (closed-open). For a normal cell that has two sets of genes, there will be nine scenarios: (1) open-open+open-open, (2) closed-closed+closed-closed, (3) open-closed+open-closed, (4) closed-open+closed-open (5) open-open+open-closed (6) open-open+closed-open, (7) open-closed+closed-closed, (8) closed-open+open-closed, (9) closed-closed+closed-open. If neither of the structural gene nor the regulator have any SNP sites to differentiate each alleles, (1), (5), (6), (8) will gave the same sequencing results upon conventional sequencing, showing as open-open. However, these four scenarios could give different expression levels. Similarly, (3) and (7) will show the same result as open-closed, and (4) and (9) will show the same result as closed-open upon conventional sequencing. Using the methods described herein, transposons with barcodes will: mark different alleles differently, based open/closed state, and make associations possible in hyploid reconstruction as illustrated in IV., so that all scenarios can be discerned.

VI. Haplotyping by Inserting Transposon Barcodes into the Continueous Strands of the Entire Genome The ability to assign multiple alleles to the same chromosome ("haplotyping") is powerful because it can provide information of clinical relevance, for example by providing information about recombination events in the genome. Such information can be important for locating mutations that cause disease and can help determine linkage disequilibrium, or the statistical association between the presence of two polymorphisms in a genome-wide disease association studies. For example, knowing the genotype at one polymorphism (e.g., SNP) can help predict the genotype of another polymorphism (e.g., SNP) if the association (i.e., linkage disequilibrium) between the two polymorphisms is high.

The ability to more completely match human leukocyte antigens (HLA) by determining their haplotypes would greatly improve the clinical outcome of, for example, transplant recipients (Crawford and Nickerson, 2004, Ann. Rev. Med. 56:303-320, incorporated herein by reference in its entirety). For example, by practicing methods described herein (see especially below), transplant recipients and potential donors could be genotyped at a plurality of markers along the major histocompatibility complex and the haplotypes could be determined from the generated data. Examples of such alignments can be found in Examples below. Such alignments could provide for highly accurate HLA matching between the transplant recipient and donor resulting in a better transplant outcome than patients and donors who are not so matched.

Additionally, there are some diseases wherein a haplotype and not a genotype at a particular locus can predict the risk and/or severity of a disease and thus aid in determining a diagnosis and/or prognosis. Furthermore, an accurate haplotype would have wide utility for determining not only the risk and/or severity of a disease for a particular patient, but also for providing a clinician with information useful in determining potential treatment options based on that diagnosis and/or prognosis, as different treatment options may correlate with different disease states and/or levels of severity. For example, a specific sickle-cell anemia β-globin locus haplotype is correlated with less severe sickle-cell anemia, and a haplotype of an IL-10 promoter region has been associated with lower incidence of graft-versus-host disease and death in patients receiving cellular transplants. As such, improved haployping methods would have a great impact on, for example, studies of disease correlation, disease diagnostic and prognostic practices, and administration of therapeutic regimens. However, haplotyping is also of great importance in agriculture and other horticultural arts, particularly in the breeding of livestock and crop plants, where diseases or advantageous properties could be correlated with particular haplotypes in an animal or plant.

Furthermore, haplotyping cancer cells by conventional methods is extremely challenging, as the chromosomes are very complex. Adding to the complexity, individual cancer cells in a cancer tissue or a cell line are heterogeneous.

Many methods exist to determine if heterozygous alleles are grouped together on a chromosome. When two alleles are not far apart, they can be easily determined by PCR, Sanger sequencing, or microarray, or NGS. However, when two alleles are far apart, haplotyping becomes challenging. Karyotyping, in situ hybridization, large-insert cloning are classical techniques for long-range haplotyping. However, they suffer from low throughput and are labor intensive.

Newer techniques suffer from one or more of the disadvantages that they are not generally applicable to any sample of interest, can be technically difficult and/or laborious to carry out, do not provide an accurate description of the genetic makeup of individual cells or representation of the heterogeneity of a cohort of cells, cannot provide accurate haplotypes for many cancer cells, and cannot be used for single-cell haplotyping.

In certain embodiments, the present invention provides a haplotyping method that overcomes all of these problems. This method entails the use of transposon-mediated barcoding to mark genomic DNA with barcodes, which can then be used to determine copy number and identify linkage between alleles (e.g., as described in sections I and IV above). An illustrative embodiment employs barcoded single-piece transposons (two transposon ends are linked and continuous), as shown in FIG. 1. The preferred target DNA is from an intact single cell. Transposition of barcoded transposons leads to the whole genome marked with barcodes in distributive manner, wherein after-nick filling, the chromosomes are kept intact and continuous. The chromosomal DNA can then be amplified in whole genome amplification, for example, using the $C_1$™ Single-Cell Auto Prep Reagent Kit for DNA Seq (Kit Part No. 100-7357), marketed by Fluidigm, Inc. The amplified, barcoded genome is then fragmented to make a library for NGS, e.g., Illumina sequencing. In contrast to prior-art haplotyping methods, production of a sequencing library can be separated from barcoding, so that the genetic makeup of a single cell, which could be unique, has a higher probability of being covered in the sequencing. By using the barcodes to get both copy number information and allele to allele linkage, accurate haploid typing is easily achievable.

Example 2: Incorporation of Barcodes into Mu Transposon Ends

This Example illustrates the incorporation of barcodes into mu transposon ends to produce artificial transposon ends that can be used in a variety of barcoding applications. The wildtype mu transposon end has the structure as shown below, followed by a set of artificial transposon ends (top strand only) including barcodes at positions 3-5. The barcoded ends are labeled TPBC1 ("transposon barcode 1") to TPBC10:

For DNA sequencing, sequencing primer, e.g., 5'-CTTTCGCGTTTTTTCGTGCGCCG-3' (SEQ ID NO:33) will prime sequencing from right to left, read the three barcode bases first, then two consensus sequence bases (5'-CA-3') of the transposon before reaching the target sequences at the sixth base.

If additional barcodes are desired, one or more of the additional underlined variable positions shown below can be used as sites for further substitutions in the mu transposon end.

```
         1                           28
5'-TGNNNYGGNGCANGNRNARYRGCGANAN-3' (SEQ ID NO: 34)
where N = any base; Y = pyrimidine; R = purine
```

Example 3: Copy Number Determination of a Gene in an Open Chromatin Region Determined by Transposon Barcodes Inserted by Tagmentation Individual K562 cells were captured at the 4.5 nL capture site of C1 according to manufacturer's instructions (www.Fluidigm.com). The cells were stained with LIVE/DEAD® Viability/Cytotoxicity Kit for mammalian cells (Cat L3224, Life Technologies, Carlsbad, Calif., USA) to be identified as live or dead under a microscope and also to determine the number of cells (0, 1, or 2) in each capture site. The cells were then washed with 1×PBS buffer, and soaked in the buffer before 9 nL of 1.5×TD buffer (Illumina), 1.5×TDE1 (Illumina), (components from Cat FC-121-1030, Illumina, San Diego, Calif., USA), 1.5% NP40 and 1.5×C1 loading reagents (Fluidigm) was delivered and mixed in the capture chamber and Reaction Chamber #1. These lysis and tagmentation reactions were allowed to proceed at 37° C. for 30 minutes. FIG. 8B represents the transposon used in this example. The tagmentation reaction was stopped in the combined the capture chambers, Reaction Chamber #1 and Reaction Chamber #2, by delivering 9 nL of 50 mM EDTA. The combined chambers were heated to 50° C. for 30 minutes. Nine nL of 50 mM $MgCl_2$ was delivered to, and mixed with, the reaction mix in the combined capture chambers, Reaction Chamber #1, #2 and #3. Finally, Phusion® PCR master mix (BioRad) with primers that contain the transposon end sequences was added to the reaction in combined the capture chamber, Reaction Chamber #1, #2,

```
                1 345                      28
        5'-TGAAGCGGCGCACGAAAAAACGCGAAAG-3'     (SEQ ID NO: 21)

3'-ACTTCGCCGCGTGCTTTTTTGCGCTTTC-5'     (SEQ ID NO: 22)

TPBC1:  5'-TGAAACGGCGCACGAAAAAACGCGAAAG-3'     (SEQ ID NO: 23)

TPBC2:  5'-TGTTACGGCGCACGAAAAAACGCGAAAG-3'     (SEQ ID NO: 24)

TPBC3:  5'-TGCCACGGCGCACGAAAAAACGCGAAAG-3'     (SEQ ID NO: 25)

TPBC4:  5'-TGGGACGGCGCACGAAAAAACGCGAAAG-3'     (SEQ ID NO: 26)

TPBC5:  5'-TGATTCGGCGCACGAAAAAACGCGAAAG-3'     (SEQ ID NO: 27)

TPBC6:  5'-TGACCCGGCGCACGAAAAAACGCGAAAG-3'     (SEQ ID NO: 28)

TPBC7:  5'-TGAGGCGGCGCACGAAAAAACGCGAAAG-3'     (SEQ ID NO: 29)

TPBC8:  5'-TGATTCGGCGCACGAAAAAACGCGAAAG-3'     (SEQ ID NO: 30)

TPBC9:  5'-TGCTGCGGCGCACGAAAAAACGCGAAAG-3'     (SEQ ID NO: 31)

TPBC10: 5'-TGCGTCGGCGCACGAAAAAACGCGAAAG-3'     (SEQ ID NO: 32)
```

3, #4, and #5. The reaction temperature was initially 70° C. for 10 minutes, followed by 10 cycles of: 95° C. for 15 seconds, 50° C. for 15 seconds and 72° C. for 2 minutes. Amplified fragments were eluted from the C1 chips and sequenced according to Illumina's protocol.

For one cell, a total of about 13000 reads of 76-base long, map-able to the positive strand of the reference genome were obtained from Illumina sequencing in low coverage. Of these reads, 10% mapped to chromosomal DNA, while 90% mapped to mitochondrial DNA. The 10% of reads that is map-able to genomic DNA includes about 30% of reads that are reads of PCR duplicates, characterized by the same starting points. Of the genomic reads, >99% of alleles were covered once. FIG. 9A shows a total of three reads obtained from a region of chromosomal DNA. However, reads 2 and 3 are identical, indicating two different transposition patterns, one for each of two alleles. FIG. 9B shows a total of 21 reads obtained from a region of mitochondrial DNA. The 21 reads include at least 7 different transposition patterns, indicating at least 7 copies of this region are present in the mitochondrial DNA. Even with limited coverage, it can be seen that the transposition pattern is proportional to the available target.

Results from another cell are shown in FIG. 10. For a region of chromosomal DNA, four different transposition patterns (Seq1-Seq4) were obtained, indicating that there are at least four copies of gene at this region. Of the four sequences, Seq1, Seq2, and Seq3 have distinct SNP sites in the overlapping region to differentiate one from the other, validating that different transposition patterns are indicating different copies of the gene. In FIG. 10, the consensus is represented in upper case, while non-consensus is represented in lower case. The arrows highlight the potential use of barcodes to discern true variants from possible sequencing error, which has been elaborated in II and IIIa.

Example 4: Copy Number Determination Using Transposon Barcodes Inserted by Tagmentation Individual single K562 cells will be captured at the 4.5 nL capture site of C1 according to manufacturer's instructions (www.Fluidigm.com). The cells will be stained with LIVE/ DEAD® Viability/Cytotoxicity Kit for mammalian cells (Cat L3224, Life Technologies, Carlsbad, Calif., USA) to be identified live or dead under a microscope. The cells will then be washed with 1×PBS buffer, and soaked in the buffer before 9 nL of 1.5×TD buffer, (components from Cat FC-121-1030, Illumina, San Diego, Calif., USA), 0.1 ug/uL, 1.5% NP40 and 1.5×C1 loading reagents will be delivered and mixed in the capture chamber and Reaction Chamber #1. These lysis and digestion reactions will be allowed to proceed at 37° C. for 30 minutes, followed by 75° C. for 30 minutes. Nine nL of 1×TD buffer with 2.5×TDE1 (FIG. 8B) will be delivered and mixed in the combined the capture chambers, Reaction Chamber #1 and #2. Tagmentation will be allowed to proceed for 5 minute at 55° C. Transposition will be stopped by delivering 9 nL of 50 mM EDTA to the combined the capture chamber, Reaction Chamber #1, #2 and #3, and increasing the temperature to 50° C. for 30 minutes. Finally, Phusion PCR master mix with primers that contain the transposon end sequences will be added to the reaction in the combined capture chamber, Reaction Chamber #1, #2, #3, #4, and #5. Reaction temperature will be first raised to 70° C. for 10 minutes, followed by 10 cycles Of: 95° C. for 15 seconds, 50° C. for 15 seconds and 72° C. for 2 minutes. Amplified fragments will be eluted from the C1 chip and sequenced according to Illumina's protocol.

The starting point of a fragment will be used to extract the barcoding information. The number of fragments of different starting points that match the same region of reference genome indicates the minimal copy number of the region of that gene.

Example 5: Insertion of Barcoded Single-Piece Transposons into the Genome

Individual single K562 cells will be captured at the 4.5 nL capture site of C1 according to manufacturer's instructions (www.Fluidigm.com). The cells will be stained with LIVE/ DEAD® Viability/Cytotoxicity Kit for mammalian cells (Cat L3224, Life Technologies, Carlsbad, Calif., USA) to be identified as live or dead under a microscope. The cells will then be washed with 1×PBS buffer, and soaked in the buffer before 9 nL of 1.5×TD buffer, (components from Cat FC-121-1030, Illumina, San Diego, Calif., USA), 0.1 ug/uL, 1.5% NP40 and 1.5×C1 loading reagents will be delivered and mixed in the capture chamber and Reaction Chamber #1. These lysis and digestion reactions will be allowed to proceed at 37° C. for 30 minutes and 75° C. for 30 minutes. Nine nL of 1×TD buffer with 2.5× barcoded 1-piece transposons (FIG. 8A) will be delivered and mixed in the combined capture chamber, Reaction Chamber #1 and #2. Transposition reactions will be allowed to proceed for 5 minute at 55° C. Transposition will be stopped, by delivering 9 nL of 50 mM EDTA to the combined the capture chamber, Reaction Chamber #1, #2 and #3, and raising the temperature to 50° C. for 30 minutes. Next, 135 nL of 1.23×DNAseq (Fluidigm) buffer containing Klenow fragment (0.1 unit/ 1000 nL), T4 DNA Ligase (0.1 unit/1000 nL) and 10 mM ATP will be delivered and mixed with the stopped transposition reaction in the combined the capture chamber, Reaction Chamber #1, #2, #3 and #4. Extension and nick-filling will be carried out for 1 hour at 25° C. Finally, 135 nL of 1×DNAseq buffer and 2.23×Phi29 (DNAseq enzyme in Fluidigm's protocol) will be delivered and mixed in the combined the capture chamber, Reaction Chamber #1, #2, #3 and #4. After 2 hours at 38° C., the whole genome amplified products will be eluted from the C1 chips according to Fluidigm's protocol, and then tagmented and sequenced according to Illumina's protocol.

Sequencing will be obtained using primers from the Read1 sequencing primer and Read2 sequencing primer. Additionally, barcoded 1-piece transposons carry primer sites for sequencing the targeted genome and barcodes.

What is claimed is:

1. A method of determining chromosome copy numbers in a genomic sample, the method comprising:
obtaining genomic DNA derived from a single fully disrupted cell;
contacting and fragmenting the genome using a loaded transposase capable of randomly incorporating transposons into the genome to form a number of fragments with transposon-nucleic acid segment combinations, wherein transposons are associated with nucleic acid segments representing genetic loci; and
detecting the number of transposon-nucleic acid segment combinations at least one locus to determine chromosome copy number.

2. The method of claim 1, wherein the different transposon-nucleic acid segment combinations comprise the same transposon sequence inserted at different sites.

3. The method of claim 1, wherein the different transposon-nucleic acid segment combinations comprise different transposon sequences inserted by different transposases.

4. The method of claim 1, wherein the transposons comprise a set of two or more transposons, wherein:
each transposon comprises a different first transposon barcode sequence;
said contacting forms barcoded nucleic acid molecules, wherein particular transposon barcodes are associated with nucleic acid segments representing the loci; and
said detecting comprises detecting the number of different transposon-nucleic acid segment combinations that comprise at least one locus.

5. The method of claim 1, wherein the transposons comprise single-stranded transposons.

6. The method of claim 4, wherein the method comprises incorporating at least 10 different barcodes into the sample nucleic acids.

7. The method of claim 1, wherein the method comprises incorporating, on average, one transposon every 200 base pairs to 400 base pairs of genomic DNA.

8. The method of claim 1, wherein a subset of the sample nucleic acids is sufficiently accessible to the loaded transposase to permit transposition and another subset is not sufficiently accessible to the loaded transposase to permit transposition.

9. The method of claim 8, wherein the sample nucleic acids comprise chromatin, and the subset of sample nucleic acids that is sufficiently accessible to the loaded transposase to permit transposition comprises nucleic acids in an open configuration in the chromatin.

10. The method of claim 8, wherein the sample nucleic acids comprise chromatin with associated methyl-CpG-binding domain (MBD) proteins, and the subset of sample nucleic acids that is not sufficiently accessible to the loaded transposase to permit transposition comprises nucleic acids in CpG islands.

11. The method of claim 1, wherein the method additionally comprises performing whole genome amplification of the nucleic acid molecules.

12. The method of claim 1, wherein said detecting comprises DNA sequencing.

13. The method of claim 12, wherein when the detected transposon-nucleic acid segment combinations comprise two different combinations wherein a nucleic acid segment comprising the same nucleic acid sequence at a detected locus is associated with one or more transposons at different insertion sites, one or more different transposon sequences, and/or one or more different barcodes, combinations thereof, permitting the sample to be identified as diploid or haploid and homozygous or heterozygous for the locus.

14. The method of claim 12, wherein when the detected transposon-nucleic acid segment combinations comprise two different transposon-nucleic acid segment combinations wherein nucleic acid segments comprising different nucleic acid sequences at a detected locus are each associated with the same transposons or barcodes at the same insertion sites, permitting the sample to be identified as one in which an error had been introduced into the sample nucleic acid sequence during amplification or sequencing.

15. The method of any of claim 12, wherein the transposons comprise barcodes, and said detection of the transposon-nucleic acid segment combinations comprises detection of barcode-nucleic acid segment combinations.

16. The method of claim 12, wherein the method comprises determining genome-wide copy number variation at a less than 10 kilobase resolution, on average.

17. The method of claim 16, wherein the method comprises determining genome-wide copy number variation at an approximately 500 base resolution, on average.

18. The method of claim 1, wherein the method additionally comprises determining whether two separated loci are present on the same chromosome, wherein one or more transposons is/are incorporated into intervening sample nucleic acid sequences to produce a transposon-nucleic acid segment combination, and the method additionally comprises analyzing the loci to determine whether both loci are linked with the same transposon-nucleic acid segment combination, wherein a determination that the loci are linked with the same transposon-nucleic acid segment combination indicates that the loci are present on the same chromosome.

19. The method of claim 18, the method additionally comprises detecting the number of different transposon-nucleic acid segment combinations that are linked to both loci to determine the copy number of the segment of genomic DNA containing both loci.

20. The method of claim 1, wherein:
said contacting comprises contacting the sample nucleic acids in a first condition with the loaded transposase in a first round of transposition to form a first set of nucleic acid molecules, wherein particular first transposons are associated with particular nucleic acid segments; and the method additionally comprises:
subjecting the first set of nucleic acid molecules, in a second condition, to a second round of transposition to form a second set of nucleic acid molecules, wherein particular second transposons are associated with particular nucleic acid segments, the second transposons being different from the first transposons; and,
for at least one locus, detecting:
the number of different transposon-nucleic acid segment combinations that comprise first transposons; and the number of different transposon-nucleic acid segment combinations that comprise second transposons.

21. The method of claim 20, wherein:
the sample nucleic acids in the first condition comprises chromatin;
the first set of nucleic acid molecules in the second condition comprises purified DNA;
the different transposon-nucleic acid segment combinations that comprise first transposons identify different alleles having an open configuration in the chromatin; and,
the different transposon-nucleic acid segment combinations that comprise second transposons identify different alleles having an open configuration in the chromatin.

22. The method of claim 20, wherein the method additionally comprises, for at least a second locus, detecting:
the number of different transposon-nucleic acid segment combinations that comprise first transposons; and
the number of different transposon-nucleic acid segment combinations that comprise second transposons.

\* \* \* \* \*

SEQUENCE LISTING

<160> NUMBER OF SEQ ID NOS: 48

<210> SEQ ID NO 1
<211> LENGTH: 25
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 1
atcggtatcg aaatccgtcc ccggt                                              25

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(16)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 2
gtatcgnnnn nnnnnnaaat ccgtccccgg t                                       31

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(19)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 3
tcggtatcgn nnnnnnnna aatccgtccc c                                        31

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(17)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 4
ggtatcgnnn nnnnnnaaaa tccgtcccc                                          29

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(19)
```

<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 5
tcggtatcgn nnnnnnnnna aatccgtccc cg                         32

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(13)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 6
tcgnnnnnnn nnnaaatccg tccccg                               26

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
atcggtatcg aaatccgtcc ccggt                                25

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(16)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 8
gtatcgnnnn nnnnnnaaat ccgtccccgg t                         31

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(19)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 9
tcggtatcgn nnnnnnnna aatccgtccc c        31

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(24)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 10
ggtatcgaaa tccgnnnnnn nnnntcccc        29

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(26)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 11
tcggtatcga aatccgnnnn nnnnnntccc cg        32

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(20)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 12
tcgaaatccg nnnnnnnnnn tccccg        26

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atcggtatcg aaatccgtcc ccggt        25

<210> SEQ ID NO 14
<211> LENGTH: 31

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(16)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 14
gtatcgnnnn nnnnnnaaat ccgtccccgg t                              31

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(19)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 15
tcggtatcgn nnnnnnnnna aatccgtccc c                              31

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggtatcgaaa tccgtcccc                                            19

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tcggtatcga aatccgtccc cg                                        22

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tcgaaatccg tccccg                                               16

<210> SEQ ID NO 19
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
agatgtgtat aagagacag                                                   19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ctgtctctta tacacatct                                                   19

<210> SEQ ID NO 21
<211> LENGTH: 28
<212> TYPE: DNA
<213> ORGANISM: Unknown
<220> FEATURE:
<223> OTHER INFORMATION: Description of Unknown: Wildtype mu transposon
      sequence

<400> SEQUENCE: 21
tgaagcggcg cacgaaaaaa cgcgaaag                                         28

<210> SEQ ID NO 22
<211> LENGTH: 28
<212> TYPE: DNA
<213> ORGANISM: Unknown
<220> FEATURE:
<223> OTHER INFORMATION: Description of Unknown: Wildtype mu transposon
      sequence

<400> SEQUENCE: 22
ctttcgcgtt ttttcgtgcg ccgcttca                                         28

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tgaaacggcg cacgaaaaaa cgcgaaag                                         28

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tgttacggcg cacgaaaaaa cgcgaaag                                         28

<210> SEQ ID NO 25
<211> LENGTH: 28
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 25
tgccacggcg cacgaaaaaa cgcgaaag                                            28

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tgggacggcg cacgaaaaaa cgcgaaag                                            28

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tgattcggcg cacgaaaaaa cgcgaaag                                            28

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tgacccggcg cacgaaaaaa cgcgaaag                                            28

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tgaggcggcg cacgaaaaaa cgcgaaag                                            28

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tgattcggcg cacgaaaaaa cgcgaaag                                            28

<210> SEQ ID NO 31
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 31
tgctgcggcg cacgaaaaaa cgcgaaag                                              28

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tgcgtcggcg cacgaaaaaa cgcgaaag                                              28

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctttcgcgtt ttttcgtgcg ccg                                                   23

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(5)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (26)..(26)
<223> OTHER INFORMATION: a, c, t, g, unknown or other
<220> FEATURE:
<221> NAME/KEY: modified_base
<222> LOCATION: (28)..(28)
<223> OTHER INFORMATION: a, c, t, g, unknown or other

<400> SEQUENCE: 34
tgnnnyggng cangnrnary rgcganan                                              28

<210> SEQ ID NO 35
<211> LENGTH: 76
<212> TYPE: DNA
```

<213> ORGANISM: Unknown
<220> FEATURE:
<223> OTHER INFORMATION: Description of Unknown: Chromosomal sequence

<400> SEQUENCE: 35
atctgctacc agtcaacccc taaaaatagc ccatgatgtc accccaaggc cttcccattg    60
gctcgcgtcg ctctca                                                   76

<210> SEQ ID NO 36
<211> LENGTH: 76
<212> TYPE: DNA
<213> ORGANISM: Unknown
<220> FEATURE:
<223> OTHER INFORMATION: Description of Unknown: Chromosomal sequence

<400> SEQUENCE: 36
cagtcaaccc ctaaaaatag cccatgatgt caccccaagg ccttcccatt ggctcgcgtc    60
gctctcaggg gggcgg                                                   76

<210> SEQ ID NO 37
<211> LENGTH: 76
<212> TYPE: DNA
<213> ORGANISM: Unknown
<220> FEATURE:
<223> OTHER INFORMATION: Description of Unknown: Mitochondrial sequence

<400> SEQUENCE: 37
aaatagccca cacgttcccc ttaaataaga catcacgatg gatcacaggt ctatcaccct    60
attaaccact cacggg                                                   76

<210> SEQ ID NO 38
<211> LENGTH: 76
<212> TYPE: DNA
<213> ORGANISM: Unknown
<220> FEATURE:
<223> OTHER INFORMATION: Description of Unknown: Mitochondrial sequence

<400> SEQUENCE: 38
gcccacacgt tccccttaaa taagacatca cgatggatca caggtctatc acctattaa    60 ccactcacgg gagctc                                                   76

<210> SEQ ID NO 39
<211> LENGTH: 76
<212> TYPE: DNA
<213> ORGANISM: Unknown
<220> FEATURE:
<223> OTHER INFORMATION: Description of Unknown: Mitochondrial sequence

<400> SEQUENCE: 39
cacacgttcc ccttaaataa gacatcacga tggatcacag gtctatcacc ctattaacca    60
ctcacgggag ctctcc                                                   76

<210> SEQ ID NO 40
<211> LENGTH: 76
<212> TYPE: DNA
<213> ORGANISM: Unknown
<220> FEATURE:
<223> OTHER INFORMATION: Description of Unknown: Mitochondrial sequence

<400> SEQUENCE: 40
ccccttaaat aagacatcac gatggatcac aggtctatca cctattaac cactcacggg    60 agctctccat gcattt                                                   76

-continued

```
<210> SEQ ID NO 41
<211> LENGTH: 76
<212> TYPE: DNA
<213> ORGANISM: Unknown
<220> FEATURE:
<223> OTHER INFORMATION: Description of Unknown: Mitochondrial sequence

<400> SEQUENCE: 41
cccttaaata agacatcacg atggatcaca ggtctatcac cctattaacc actcacggga      60
gctctccatg catttg                                                     76

<210> SEQ ID NO 42
<211> LENGTH: 76
<212> TYPE: DNA
<213> ORGANISM: Unknown
<220> FEATURE:
<223> OTHER INFORMATION: Description of Unknown: Mitochondrial sequence

<400> SEQUENCE: 42
ttaaataaga catcacgatg gatcacaggt ctatcaccct attaaccact cacgggagct      60
ctccatgcat ttggta                                                     76

<210> SEQ ID NO 43
<211> LENGTH: 76
<212> TYPE: DNA
<213> ORGANISM: Unknown
<220> FEATURE:
<223> OTHER INFORMATION: Description of Unknown: Mitochondrial sequence

<400> SEQUENCE: 43
aaataagaca tcacgatgga tcacaggtct atcaccctat taaccactca cgggagctct      60
ccatgcattt ggtatt                                                     76

<210> SEQ ID NO 44
<211> LENGTH: 150
<212> TYPE: DNA
<213> ORGANISM: Unknown
<220> FEATURE:
<223> OTHER INFORMATION: Description of Unknown: Chromosomal sequence

<400> SEQUENCE: 44
ctctgtttgt caagtctgca agtggatatt cggacctctt tgaggccttc gttggaaacg      60
ggatttcttc atattacact agacagaaga attctcagta acttcctttt gttgtgtgta     120
ttcaactgac agagttgaac cttcccttag                                     150

<210> SEQ ID NO 45
<211> LENGTH: 76
<212> TYPE: DNA
<213> ORGANISM: Unknown
<220> FEATURE:
<223> OTHER INFORMATION: Description of Unknown: Chromosomal sequence

<400> SEQUENCE: 45
ctctgtttgt aaactctgca agtggatatt cagacctctt tgaggccttc gttggaaacg      60
ggatttcttc atacta                                                     76

<210> SEQ ID NO 46
<211> LENGTH: 76
<212> TYPE: DNA
<213> ORGANISM: Unknown
<220> FEATURE:
```

```
<223> OTHER INFORMATION: Description of Unknown: Chromosomal sequence

<400> SEQUENCE: 46
gtggatattc agacctcttt gaggcctaag ttggaaacgg gatttcttca tactatgcta        60
gacagaagaa ttctca                                                        76

<210> SEQ ID NO 47
<211> LENGTH: 76
<212> TYPE: DNA
<213> ORGANISM: Unknown
<220> FEATURE:
<223> OTHER INFORMATION: Description of Unknown: Chromosomal sequence

<400> SEQUENCE: 47
atattcagac ctctttgagg ccttcgttgg aaacgggttt ttttcatata aggctagaca        60
gaagaattcc cagtaa                                                        76

<210> SEQ ID NO 48
<211> LENGTH: 76
<212> TYPE: DNA
<213> ORGANISM: Unknown
<220> FEATURE:
<223> OTHER INFORMATION: Description of Unknown: Chromosomal sequence

<400> SEQUENCE: 48
ccttcgttgg aaacgggatt tcttcatact atgctagaca gaagaattct cagtaacttc        60
cttgtgttgt gtgtat                                                        76
```